United States Patent [19]
Collins et al.

[11] Patent Number: 6,077,708
[45] Date of Patent: Jun. 20, 2000

[54] METHOD OF DETERMINING PROGENITOR CELL CONTENT OF A HEMATOPOIETIC CELL CULTURE

[76] Inventors: Paul C. Collins, 785 W. Foothill Rd., Bridgewater, N.J. 08807; E. Terry Papoutsakis, 706 Waukegan Rd., Unit 404, Glenview, Ill. 60025; William M. Miller, 2204 Asbury Ave., Evanston, Ill. 60201

[21] Appl. No.: 09/160,457

[22] Filed: Sep. 24, 1998

Related U.S. Application Data

[63] Continuation-in-part of application No. 09/116,853, Jul. 16, 1998, abandoned.
[60] Provisional application No. 60/052,958, Jul. 18, 1997, and provisional application No. 60/059,811, Sep. 24, 1997.
[51] Int. Cl.[7] .............................. C12N 5/00; C12N 5/08
[52] U.S. Cl. ......................... 435/375; 435/14; 435/325; 435/372.2; 435/372.3; 436/14; 436/62
[58] Field of Search .................................. 435/325, 372, 435/372.2, 372.3, 375, 289.1, 14; 436/14, 62

[56] References Cited

PUBLICATIONS

Bainton et al., *J. Exp. Med.*, 134, 907–934 (1971).
Beck et al., *Cancer Res.*, 12, 823–828 (1952).
Beck et al., *Cancer Res.*, 12:818–822 (1952).
Beck, *J. Biol. Chem.*, 232:251–270(1958).
Bender et al., *J. Hematotherapy*, 1:329–341 (1992).
Bertolini et al., *Blood*, 89:2679–2688 (1997).
Bird et al. *Cancer*, 1009–1014 (1951).
Brugger et al., *New Engl. J. Med.*, 333:283–287 (1995).
Cannistra et al., *J. Biol. Chem.*, 265(21):12656–12663 (1990).
Cannistra et al., *Proc. Nat'l Acad. Sci.*, 87:93–97 (1990).
Cline, in *Formation and Destruction of Blood Cells*, pp. 222–239 (Greenwalt and Jamieson eds., 1970).
Collins et al., Glucose and Lactate Metabolic Rates Predict Numbers of Colony–Forming Cells in Hematopoietic Culture, Abstract 2417, pub. Nov. 15, 1996.
Collins et al., *Biotechnol. Bioeng.*, 55:693–700 (1997).
Collins et al., *Biotechnol. Prog.*, 14:466–472 (1998).
Collins et al., *Biotechnol. Bioeng.*, 59:534–43 (1998).
DiPersio et al., *J. Biol. Chem.*, 263(4):1834–41 (1988).
Gesinski et al., *Australian Journal of Biological Sciences*, 21:1319–1324 (1968).
Gore et al., *Exp. Hematol.*, 23:413–421 (1995).
Hamilton et al., *Biochem. Biophys. Res. Commun.*, 138:445–454 (1986).
Hamilton et al., *J. Cell. Physiol.*, 134:405–412 (1988).
Haylock et al., in: Hematopoietic stem cells: biology and therapeutic applications (D. Levitt et al., eds., Marcel Dekker, Inc., New York, pp. 491–517 (1995).
Hedeskov, *Biochem. J.*, 110:373–380 (1968).
Hume et al., *J. Natl. Cancer Inst.*, 62:3–8 (1979).
Kester et al., *Arch. Biochem. Biophys.*, 183:700–709 (1977).
Koller et al., *Exp. Hematol.*, 20:264–270 (1992).
Koller et al., *Biotechnol. Bioeng.*, 50:505–513 (1996).
Koller et al., *Ann. New York Acad. Sci.*, 665:105–116 (1992).
Koller et al., *Blood*, 80:403–411 (1992).
Laluppa et al., *Exp. Hematol.*, 26:835–843 (1998).
Laluppa, *J. Biomed. Mat. Res.*, 36:347–359 (1997).
Lanks et al., *J. Cell. Physiol.*, 135:151–155 (1988).
Lutton et al., *Experientia*, 28:850 (1972).
McAdams et al., *Trends Biotechnol.*, 14:341–349 (1996).
McAdams et al., *Trends Biotechnol.*, 14:388–396 (1996).
Miller et al., *J. Cell. Physiol.*, 132:524–530 (1987).
Miller et al., *Bioprocess Engineering* 3:103–111 (1988).
Newsholme, et al., *Biosci. Rep.*, 5:393–400 (1985).
Olander, *American Journal of Physiology*, 222:45–48 (1972).
Peng et al., *Annals of Biomedical Engineering*, 24:373–381 (1996).
Pierson et al., *J. Hematotherapy*, 5:475–483 (1996).
Rogers et al., *Ann. Hum. Genet.*, 43:213–226 (1980).
Sand et al., *Blood*, 50:337–346 (1977).
Sardonini and Wu, *Biotechnol. Prog.*, 9:131–137 (1993).
Spielholz et al., *Blood*, 85:973–980 (1995).
Testa et al., *Blood*, 88(9):3391–3406 (1996).
Traycoff et al., *Exp Hematol*, 22:1264–1272 (1994).
Whetton et al., *EMBO J.*, 3:409–413 (1984).
Whetton, et al., *J. Cell Sci.*, 84:93–104 (1986).
Williams et al., *Blood.*, 87:1687–1691 (1996).
Zandstra et al., *Bio/Technology*, 12:909–914 (1994).
Zandstra et al., *Biotechnol. Bioeng.*, 54:58–66 (1997).
Zhou et al., *Biotechnol. Bioeng.*, 44:170–177 (1994).

*Primary Examiner*—Prema Mertz
*Assistant Examiner*—Fozia Hamud
*Attorney, Agent, or Firm*—Sheridan Ross

[57] ABSTRACT

The invention provides a method of determining the content of progenitor cells in a hematopoietic cell culture. The method comprises measuring one or more metabolic parameters of the culture, such as oxygen consumption, glucose consumption and/or lactate production, and using the measured parameter(s) to determine the content of progenitor cells.

20 Claims, 19 Drawing Sheets

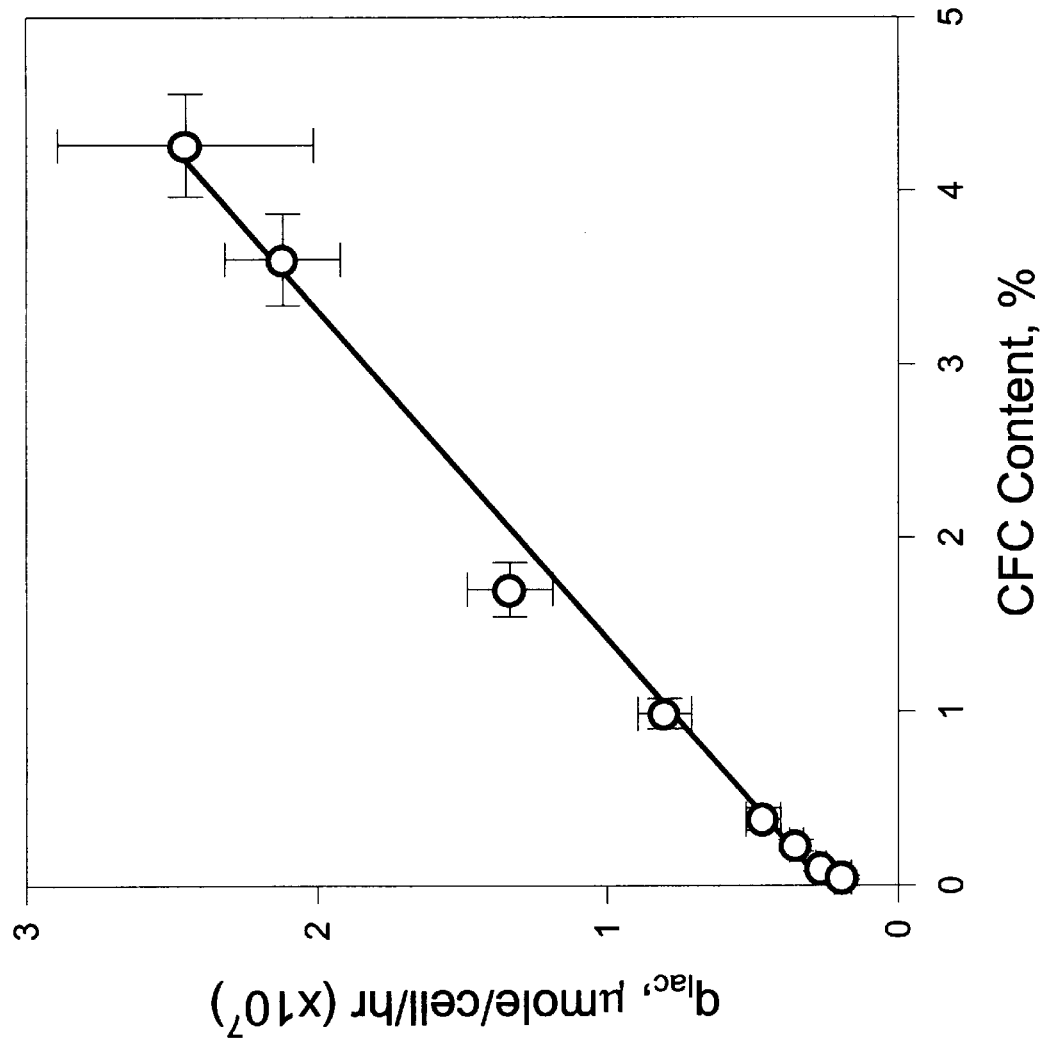

METHOD OF DETERMINING PROGENITOR CELL CONTENT OF A HEMATOPOIETIC CELL CULTURE

This application is a continuation-in-part of application No. 09/116,853 filed Jul. 16, 1998 now abandoned. Also, benefit of provisional applications No. 60/052,958, filed Jul. 18, 1997, and 60/059,811, filed Sep. 24, 1997, is hereby claimed.

This invention was made with government support under National Science Foundation Grant BES-9410751 and National Institutes Of Health Predoctoral Biotechnology Training Grant GM08449. The government may have certain rights in the invention.

FIELD OF THE INVENTION

The invention relates to methods of determining the content of progenitor cells (also referred to as colony forming cells) in a hematopoietic cell culture. The method of the invention utilizes measurements of one or more metabolic parameters of the culture, such as glucose consumption, oxygen consumption, and lactate production, to determine the progenitor cell content.

BACKGROUND

The culture of hematopoietic cells for transplantation therapies is a rapidly growing area of biotechnology and experimental hematology. As evidenced by recent clinical trials (Brugger et al., *New Engl. J. Med.*, 333, 283–287 (1995); Williams et al., *Blood*, 87, 1687–1691 (1996); Bertolini et al., *Blood*, 89, 2679–2688 (1997)), ex vivo expanded hematopoietic cells offer great promise for the reconstitution of in vivo hematopoiesis in patients who have undergone chemotherapy. Other potential applications for ex vivo expansion include production of cycling stem and progenitor cells for gene therapy, expansion of dendritic cells for immunotherapy, and production of red blood cells and platelets for transfusions (McAdams et al., *Trends Biotechnol.*, 14, 388–396 (1996)). Thus, it is likely that the demand for ex vivo expanded hematopoietic cells will increase dramatically.

Hematopoietic cultures are among the most challenging culture systems. The heterogeneous cell population contained in a hematopoietic culture is always changing as a result of the delicate balance between proliferation of certain cell types, their differentiation into other cell types, and the death of various cell populations. The lifespan of cells in culture is likely to depend on cytokine stimulation, as well as on a number of physicochemical parameters, such as pH, dissolved oxygen, and nutrient and metabolite concentrations (McAdams et al., *Trends Biotechnol.*, 14, 341–349 (1996)).

Current enumeration techniques for hematopoietic cultures do not provide real-time analysis of the changing populations. Complete evaluation of the performance of hematopoietic cultures requires the use of assays with long durations, such as the two-week methylcellulose assay to detect progenitor or colony-forming cells (CFC), including colony-forming units-granulocyte/monocyte (CFU-GM) and burst-forming units-erythroid (BFU-E), and the seven-week assay for the very primitive long-term culture-initiating cells (LTC-IC). In this regard, the cell requirements for successful engraftment are often expressed in terms of the number of CFC transplanted (e.g., $2 \times 10^5$ CFU-GM per kg body weight; Bender et al., *J. Hematotherapy*, 1, 329–341 (1992)). In contrast to the long assay times, the time period available to determine when to harvest ex-vivo cultures for transplantation therapies is most likely on the order of hours. Currently, only flow cytometry offers this speed of analysis. Flow cytometry can be utilized to quantify cells bearing antigens such as CD34 (primitive progenitors), CD15 and CD11b (granulocyte and monocyte post-progenitors), and gly A (maturing erythrocytes). Even so, sample preparation and measurement, along with data analysis, requires 2–3 hours. Furthermore, when cells bearing the antigen of interest are present at a low concentration, as is often the case for CFC, accurate quantitation may be difficult. Also, it should be noted that, although most CFC present in hematopoietic cell sources (e.g., bone marrow or umbilical cord blood) express the CD34 antigen, CD34 expression by cultured cells is often lost before the CFC content of a culture is depleted. Because of the difficulty in determining when CFU-GM, BFU-E, or other cell populations of interest reach a maximum level, culture endpoints have generally been chosen based on a retrospective analysis of the culture duration that usually yields an acceptable product. While the use of retrospective analysis may be adequate, it is far from optimal due to the heterogeneity in the kinetics of cell expansion (e.g., initial quiescent phase and the time at which various cell populations reach a maximum) for different hematopoietic cell source samples.

Nutrient consumption and by-product accumulation rates are parameters that can be readily measured in real-time. These rates are frequently employed for the control of more traditional cell cultures (for vaccine and protein production), but have been largely overlooked in the evaluation of hematopoietic cultures.

Normal and leukemic human blood cells depend heavily upon glycolysis as their source of energy (Beck, *J. Biol. Chem.*, 232, 251–270 (1958); Beck and Valentine, *Cancer Res.*, 12, 818–822 (1952); Beck and Valentine, *Cancer Res.*, 12, 823–828 (1952)), and the rates of glucose consumption and lactate production can be altered by external stimuli, such as growth factors. Growth factor-stimulated increases in glucose utilization have been demonstrated in cultures of murine macrophages (Hamilton et al., *Biochem. Biophys. Res. Commun.*, 138, 445–454 (1986)) and multipotential hematopoietic cell lines (Whetton et al., *EMBO J.*, 3, 409–413 (1984); Whetton, et al., *J. Cell Sci.*, 84, 93–104 (1986)). Human lymphocytes stimulated to undergo blastogenesis by incubation with phytohemagglutinin (PHA) exhibit increased glucose utilization and lactate production and increased levels of glycolytic pathway enzymes (Hedeskov, *Biochem. J.*, 110, 373–380 (1968); Rogers et al., *Ann. Hum. Genet.*, 43, 213–226 (1980); Kester et al., *Arch. Biochem. Biophys.*, 183, 700–709 (1977)). The findings discussed above for stimulated hematopoietic cells are consistent with those for rapidly dividing cells in general, which are known to exhibit rates of glucose consumption and lactate production that are elevated over those of more slowly growing cells (Hume and Weidemann, *J. Natl. Cancer Inst.*, 62, 3–8 (1979); Newsholme, et al., *Biosci. Rep.*, 5, 393–400 (1985); Lanks and Li, *J. Cell. Physiol.*, 135, 151–155 (1988)). Data regarding oxygen consumption rates in human hematopoietic cultures are scarce, and the published reports have not fully examined the effects of various cell populations on oxygen metabolism. Peng and Palsson (*Annals Of Biomedical Engineering*, 24, 373–381 (1996)) examined oxygen uptake by human bone marrow cells in modified six-well culture plates. They found that the specific oxygen uptake rate (moles per cell per hour) increased steadily during the first 10 days in culture and then remained steady or increased slightly from days 10–14. Bird et al.

(*Cancer*, 1009–1014 (1951)) measured oxygen uptake by normal human granulocytes.

SUMMARY OF THE INVENTION

In view of the foregoing, it was expected, in a hematopoietic culture containing cells with varying proliferative potential and rates of growth, that metabolic parameters of the culture, such as glucose consumption, oxygen consumption and lactate production, would vary directly with total cell density as proliferation and differentiation occurred. Instead, it has surprisingly been discovered that the metabolic parameters of a hematopoietic cell culture correlate with the progenitor cell (colony forming cell) content of such a culture.

Accordingly, the invention provides a method of determining the content of progenitor cells in a hematopoietic cell culture. The method comprises culturing a reference culture of hematopoietic cells under selected conditions. At least one metabolic parameter of the reference culture is measured at a plurality of selected times. Also, the content of progenitor cells in the reference culture is determined at each of the selected times. Then, an experimental culture of hematopoietic cells is cultured under essentially the same conditions used to culture the reference culture, and the same metabolic parameter(s) as was(were) measured for the reference culture is(are) measured for the experimental culture at a selected time. Finally, the metabolic parameter (s) measured for the experimental culture is(are) compared with that (those) measured for the reference culture to determine the content of the progenitor cells in the experimental culture at the selected time.

BRIEF DESCRIPTION OF THE DRAWINGS

FIG. 7: Graph of $q_{lac}$ vs. % CFC for a CB MNC culture carried out in a spinner flask at an ID of 250,000 cells/ml in HLTM plus IL-3, IL-6, SCF, G-CSF, GM-CSF, and Epo. The correlation coefficient for the line is 0.99. The error bars indicate the mean±one standard deviation. Standard deviations were determined by propagation of the errors in cell density (5%), lactate concentration (2% or 5%), and CFC ( $$\frac{\sqrt{N}}{N},$$

where N is the total number of colonies counted) through the calculations for $q_{lac}$ and % CFC.

Figure 8A:
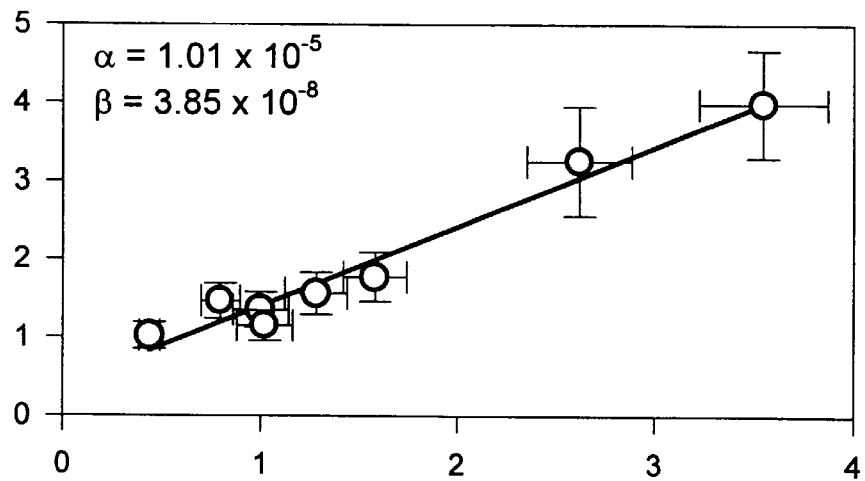
Figure 8B:
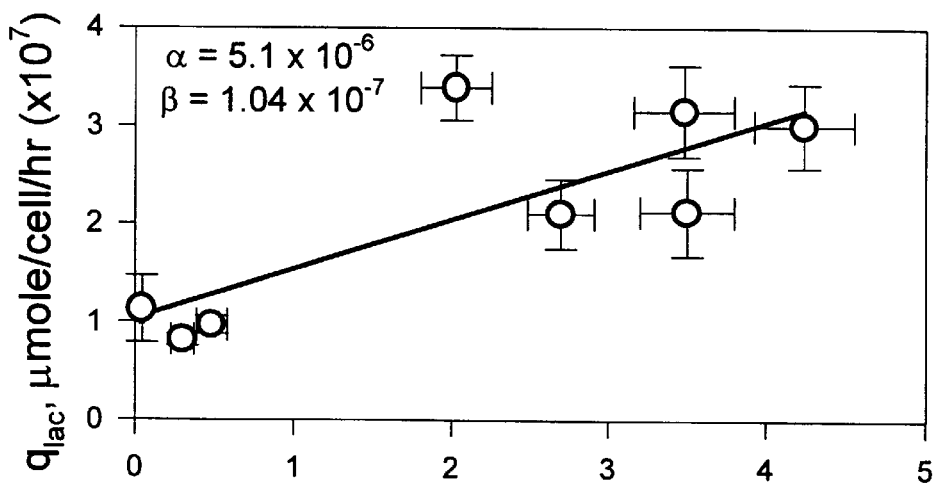
Figure 8C:
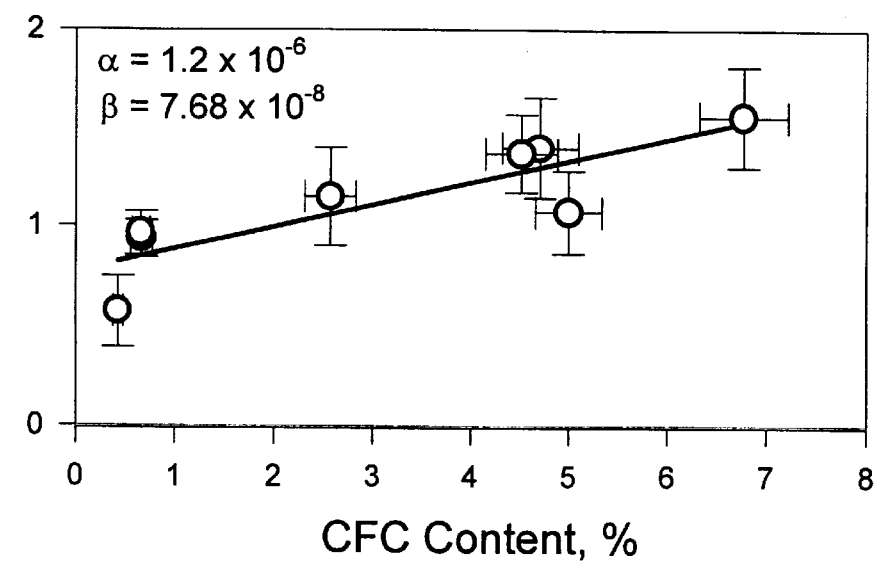

FIGS. 8A–C: Graph of $q_{lac}$ vs. % CFC in spinner flasks for a single PB MNC sample cultured at an ID of 160,000 cells/ml (FIG. 8A), 750,000 cells/ml (FIG. 8B), and 1,260, 000 cells/ml (FIG. 8C). The cultures were carried out in HLTM plus IL-3, IL-6, SCF, G-CSF, GM-CSF, and Epo. The data are the same as those shown in time-course format in FIG. 3. The correlation coefficients for the lines are: 0.96 (FIG. 8A), 0.63 (FIG. 8B), and 0.74 (FIG. 8C). The error bars indicate the mean±one standard deviation and were determined as described for FIG. 7. The value of α was $4.66 \times 10^{-7}$, and the value of β was $3.41 \times 10^{-8}$.

Figures 9A, 9B, 9C:
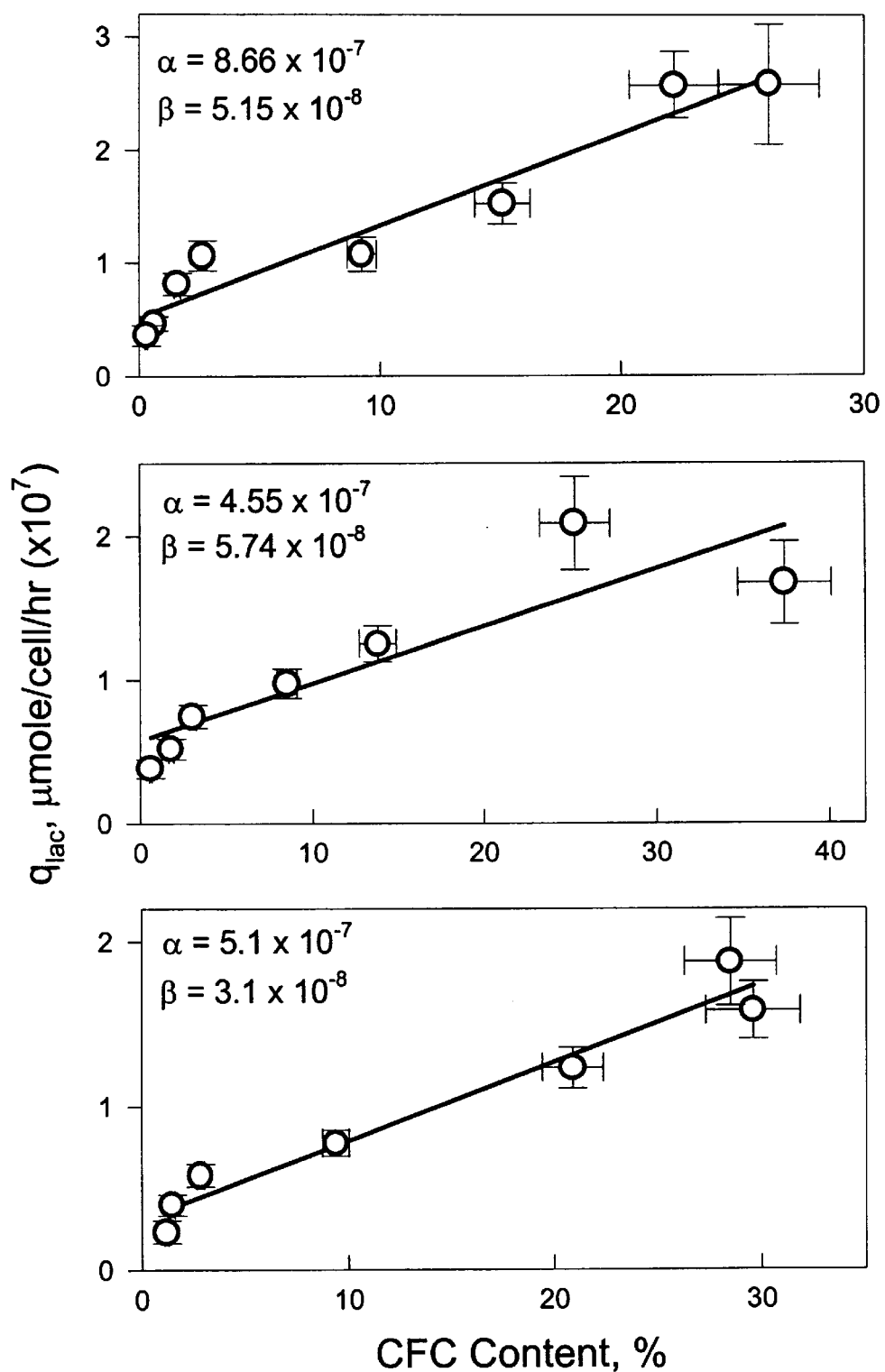

FIGS. 9A–C: Graph of $q_{lac}$ vs. % CFC in T-flasks for a single PB CD34+ cell sample cultured at an ID of 33,000 cells/ml (FIG. 9A), 82,000 cells/ml (FIG. 9B), and 125,000 cells/ml (FIG. 9C). The cultures were carried out in HLTM plus IL-3, IL-6, SCF, G-CSF, GM-CSF, and Epo. The data are the same as those shown in time-course format in FIG. 6, except that the first time point has been deleted from each culture. The correlation coefficients for the lines are 0.94 (FIG. 9A), 0.79 (FIG. 9B), and 0.95 (FIG. 9C). The error bars indicate the mean±one standard deviation and were determined as described for FIG. 7.

Figure 10:
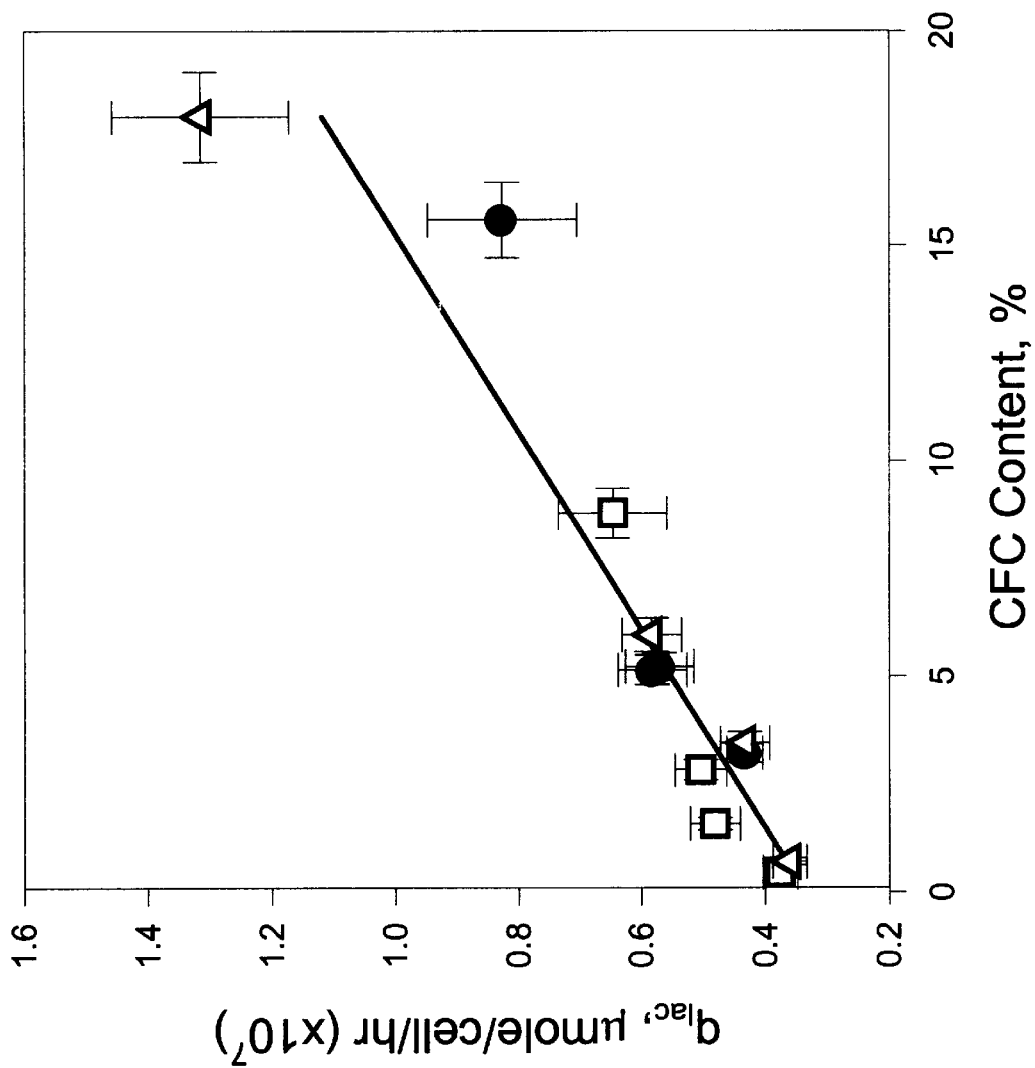

FIG. 10: Graph of $q_{lac}$ vs. % CFC for three PB MNC cultures carried out in spinner flasks with HLTM plus IL-3, IL-6, SCF, G-CSF, GM-CSF, and Epo at an ID of $1.2 \times 10^6$ cells/ml. The day zero CD34+ cell content of the samples were 6.6% (●), 6.3% (□), and 5.8% (Δ). The correlation coefficient for the line is 0.88. The error bars indicate the mean±one standard deviation and were determined as described in FIG. 7.

Figures 11A, 11B:
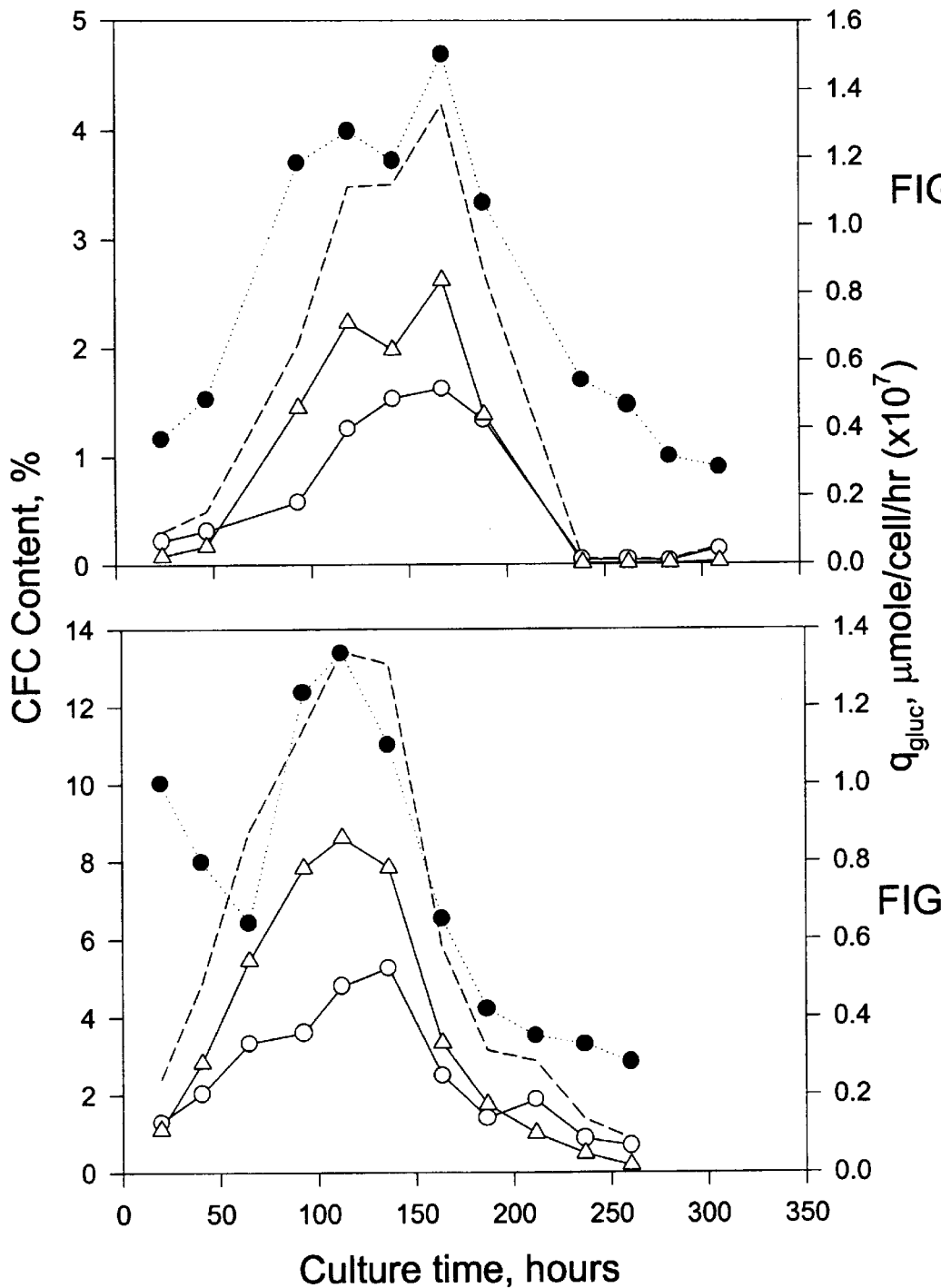

FIGS. 11A–B: Time profiles for $q_{gluc}$ and the % of cells that are CFU-GM, BFU-E and total CFC for a PB MNC sample cultured at an ID of 700,000 cells/ml (FIG. 11A) and 450,000 cells/ml (FIG. 11B). All cultures were carried out with IL-3, IL-6, SCF, G-CSF, GM-CSF, and Epo in either HTIM medium (FIG. 11A) or XVIVO-20 medium (FIG. 11B). In FIGS. 11A–B, ○=%GM, Δ=%, ●=% CFC, and the dashed line is $q_{gluc}$.

Figure 12A:
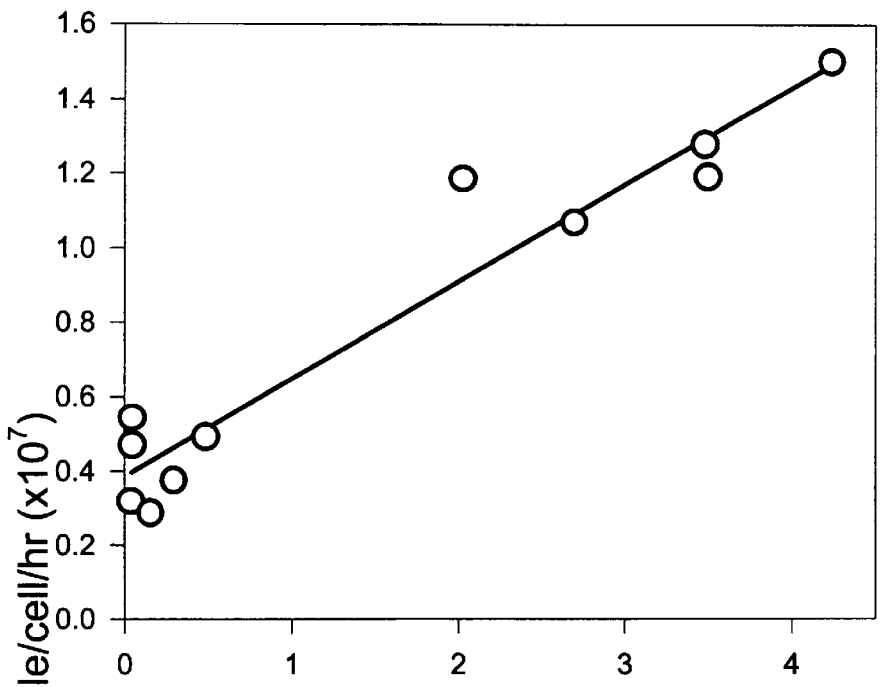
Figure 12B:
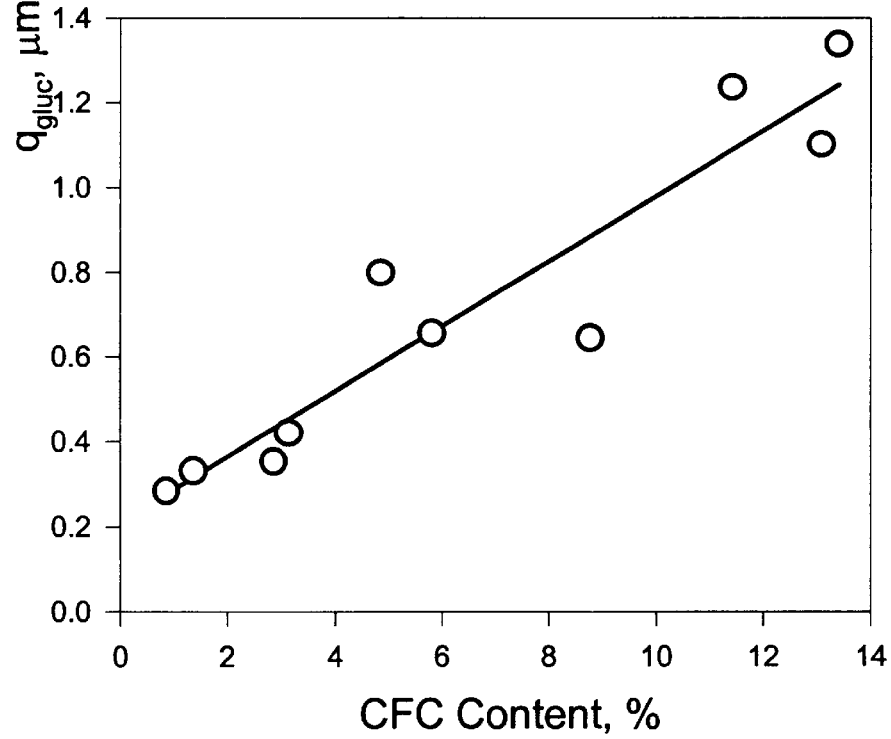

FIGS. 12A–B: Graph of $q_{gluc}$ vs. % CFC for the same cultures as FIGS. 11A–B. ID of 700,000 cells/ml in HTLM medium (FIG. 11A), and ID of 450,000 cells/ml in XVIVO-20 medium (FIG. 11B). In FIG. 12A,, y=2.61E–06x+3.86E–

08 and $R^2$=9.28E–01; and in FIG. 12B, y=7.69E–07x+ 2.11E–08 and $R^2$=8.86E–01.

Figure 13A:
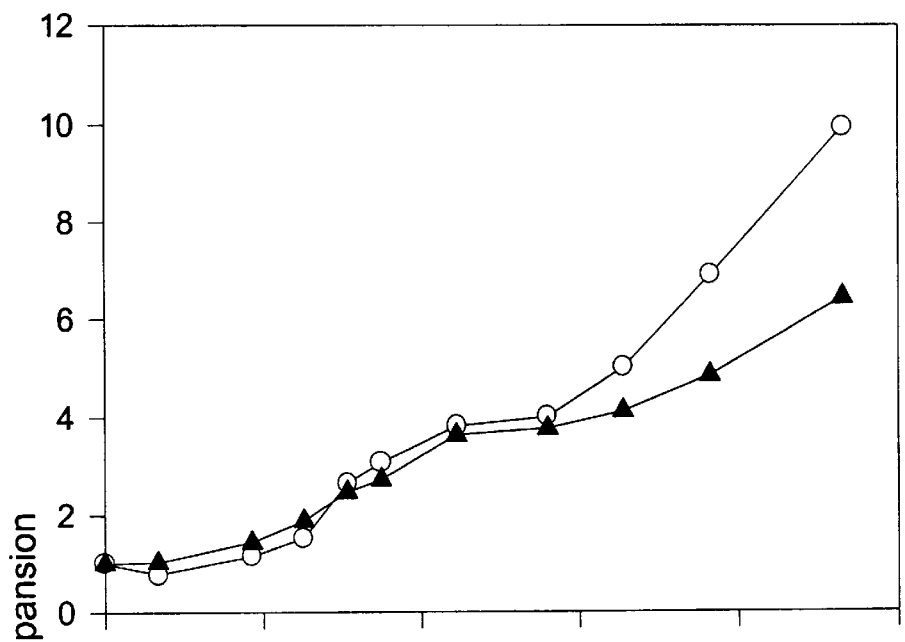
Figure 13B:
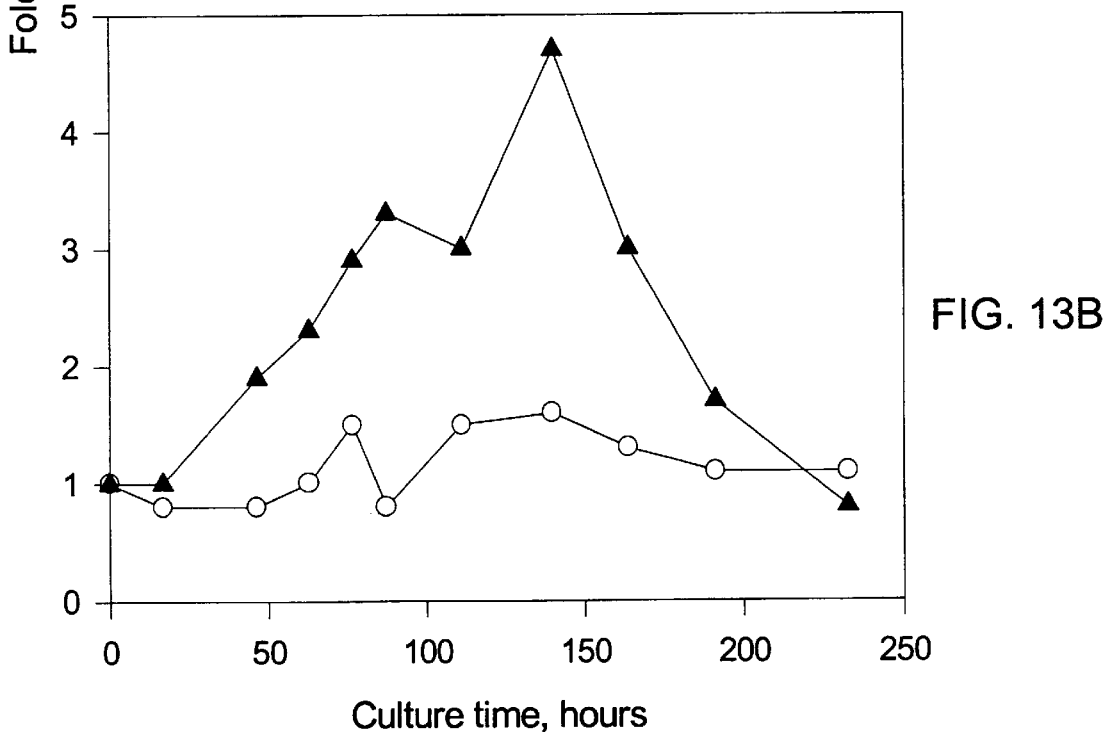

FIGS. 13A–B: Time profiles for the expansion of total cells (FIG. 13A) and CFU-GM (FIG. 13B) for a single CB MNC sample (Experiment 1) cultured in a T-flask (-▲-) and a bioreactor (-◯-) at an ID of $1.37 \times 10^6$ cells/ml. The final culture density was $6.2 \times 10^6$ cells/ml in the bioreactor and $8.8 \times 10^6$ cells/ml in the T-flask. The cultures were conducted in HLTM with IL-3, IL-6, SCF, G-CSF, GM-CSF, and Epo and were fed using a cell-retention feeding protocol (FP1), except that the bioreactor was diluted from $5.2 \times 10^6$ to $3.2 \times 10^6$ cells/ml at 144 hours.

Figure 14:
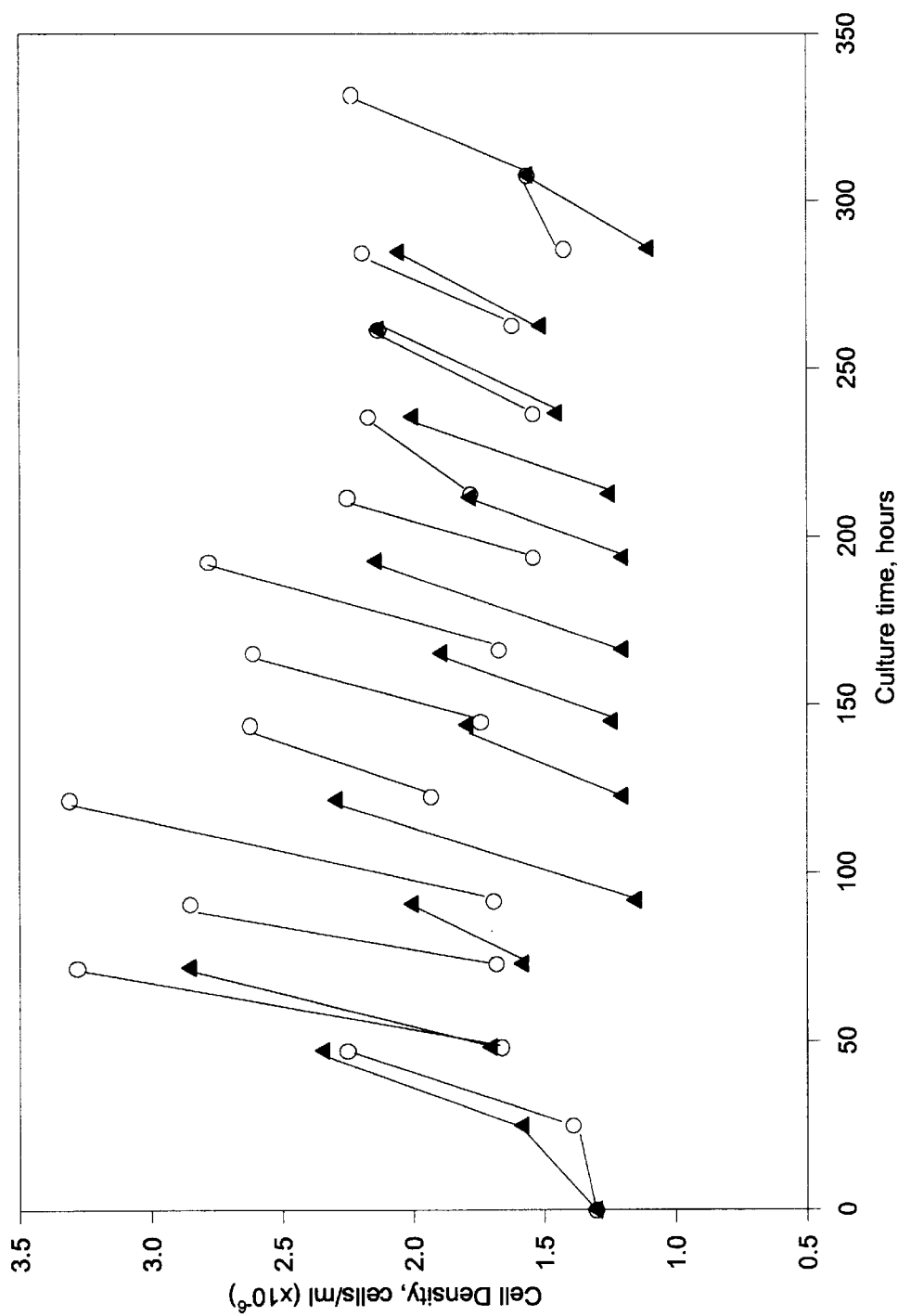

FIG. 14: Time profile of the cell density for a single CB MNC sample (Experiment 3) cultured in a T-flask (-▲-) and in a bioreactor (-◯-) at an ID of $1.3 \times 10^6$ cells/ml. The cultures were conducted in HLTM with IL-3, IL-6, SCF, G-CSF, GM-CSF, and Epo and were fed using a dilution feeding protocol (FP2).

Figures 15A, 15B, 15C:
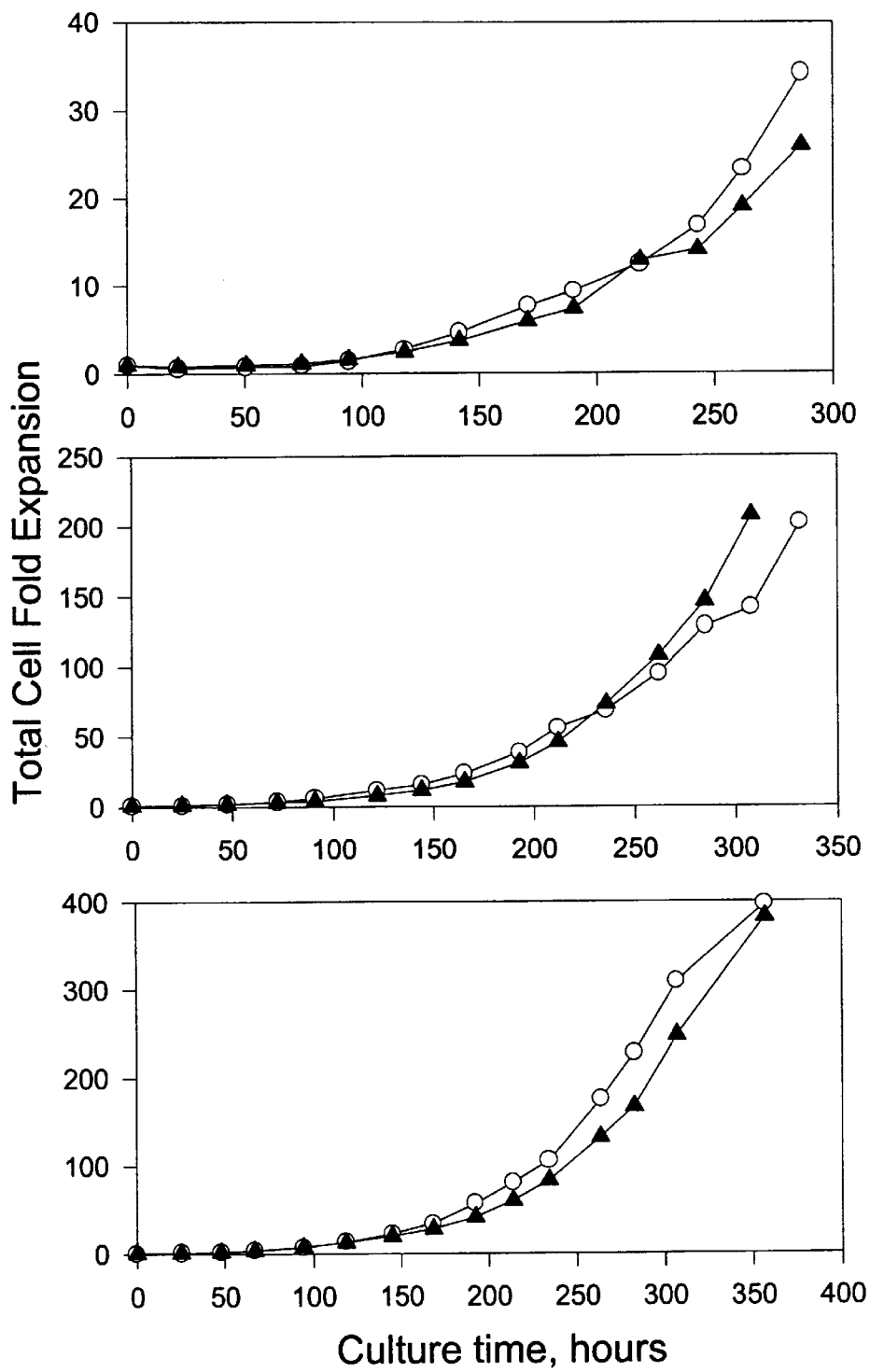

FIGS. 15A–C: Time profiles for total cell expansion in a T-flask (-▲-) and a bioreactor (-◯-) using FP2 for Experiment 2 (CB MNC, ID=$1.72 \times 10^6$ cells/ml) (FIG. 15A), Experiment 3 (CB MNC, ID=$1.3 \times 10^6$ cells/ml) (FIG. 15B), and Experiment 4 (PB MNC, ID=$2.24 \times 10^5$ cells/ml) (FIG. 15C).

Figures 16A, 16B, 16C:
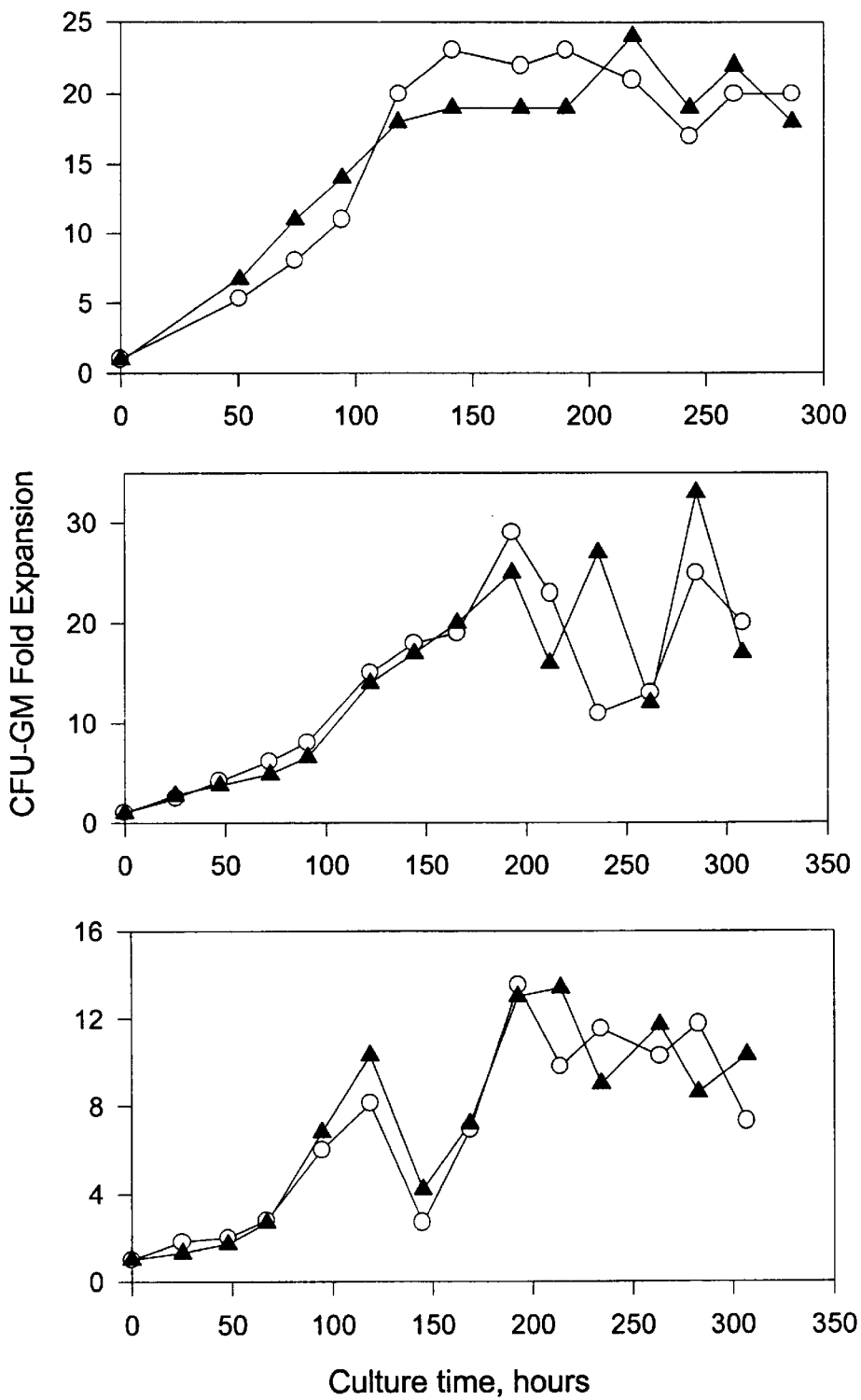

FIGS. 16A–C: Time profiles for CFU-GM expansion in a T-flask (-▲-) and a bioreactor (-◯-) with FP2 for Experiment 2 (FIG. 16A), Experiment 3 (FIG. 16B), and Experiment 4 (FIG. 16C).

Figures 17A, 17B, 17C, 17D:
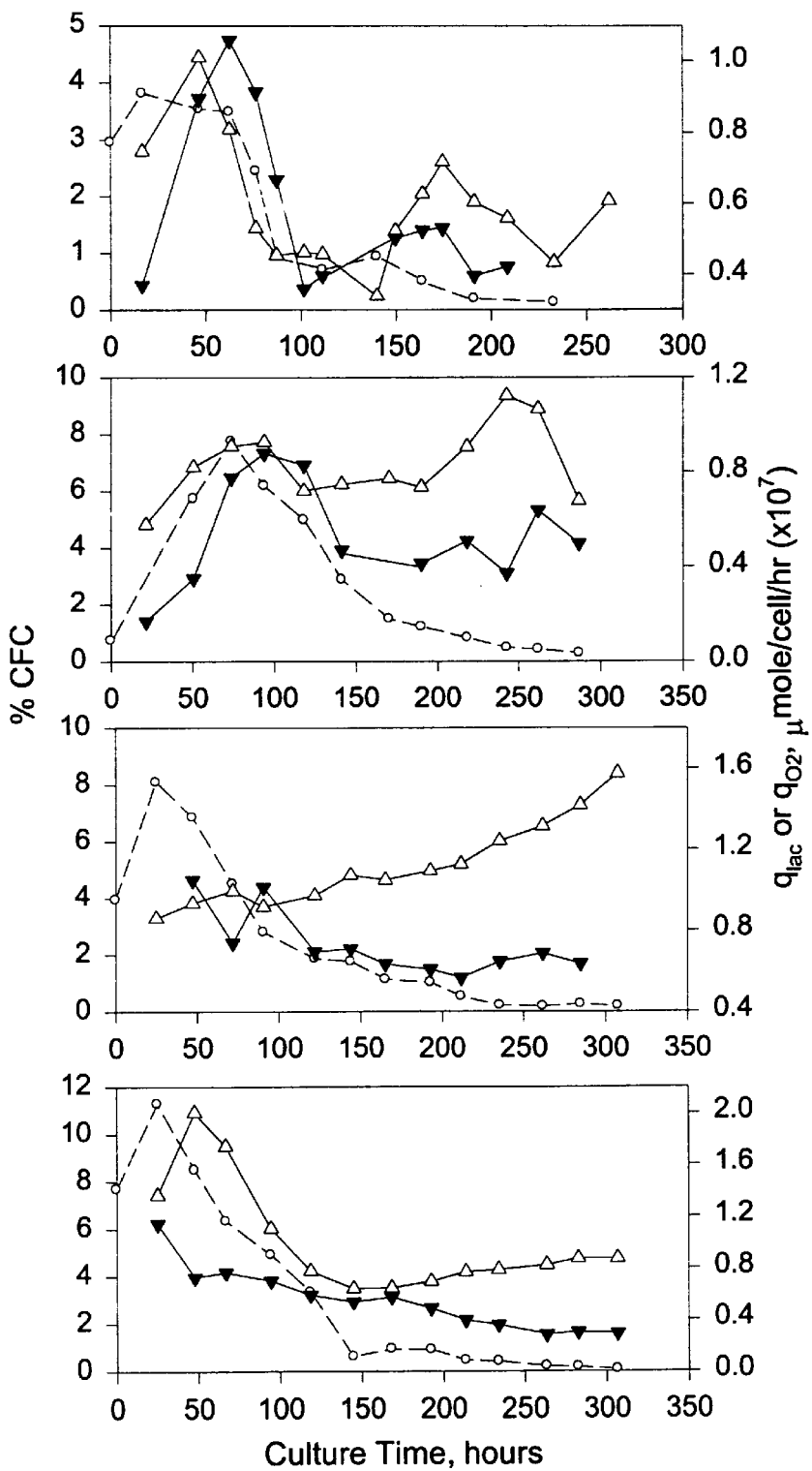

FIGS. 17A–D: Time profiles for % CFC (-◯-), $q_{lac}$ (-△-), and $q_{O2}$ (-▼-) for Experiment 1 (FIG. 17A), Experiment 2 (FIG. 17B), Experiment 3 (FIG. 17C), and Experiment 4 (FIG. 17D).

Figures 18A, 18B, 18C, 18D:
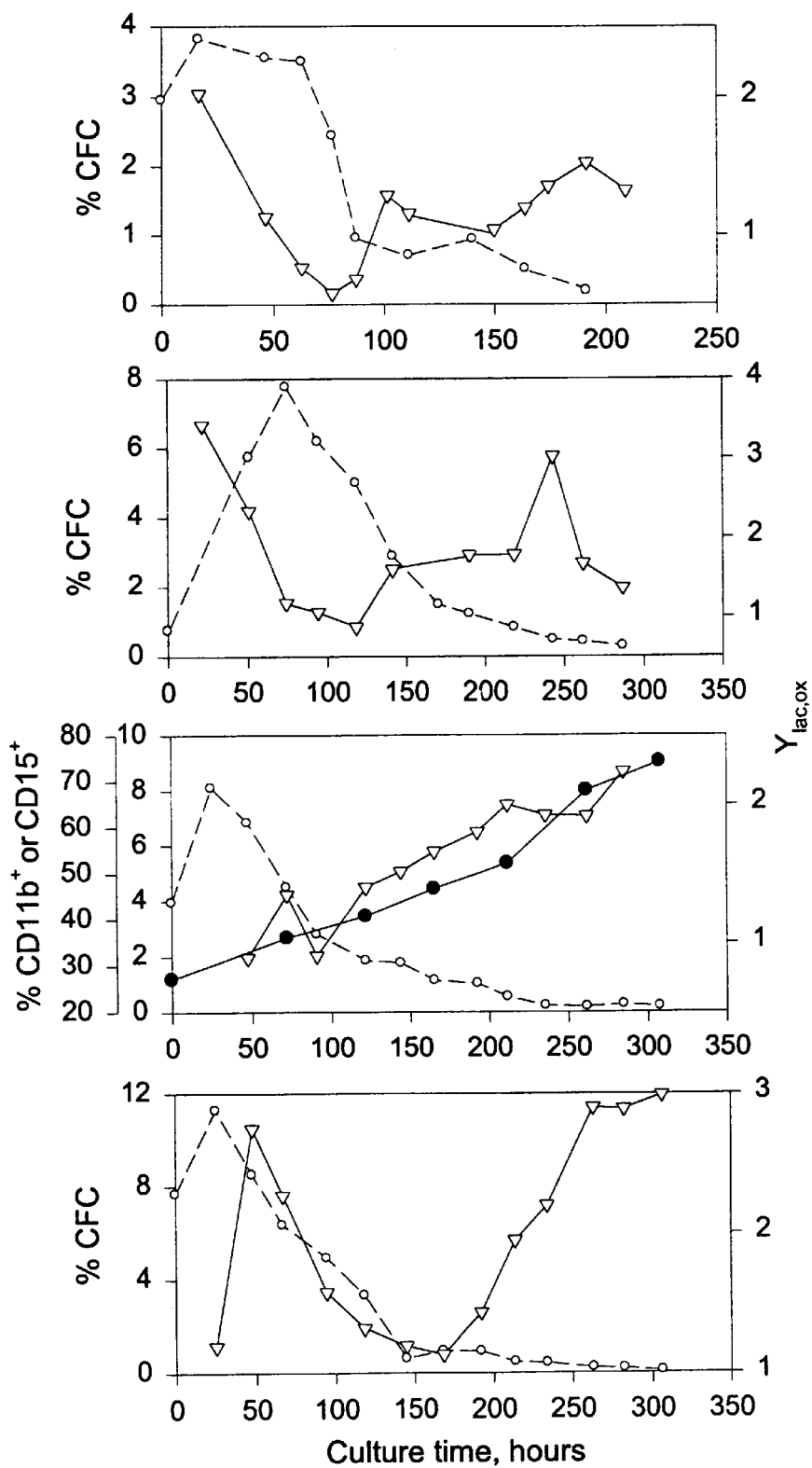
Figures 19A, 19B, 19C, 19D:
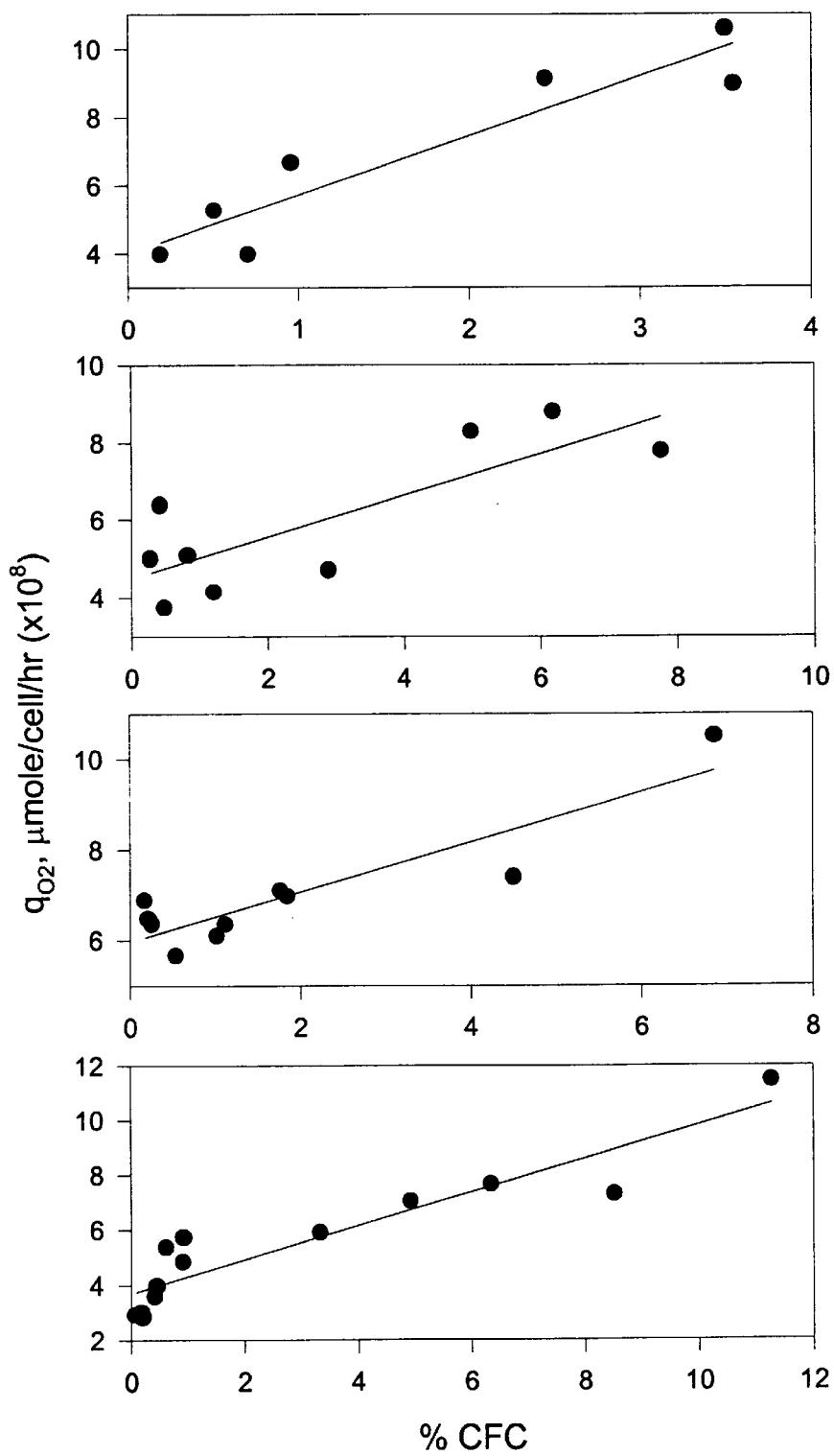

FIGS. 18A–D: Time profiles for % CFC (-◯-), $Y_{lac,ox}$ (-▽-), and % CD11b$^+$ and/or CD15$^+$ cells (-●-) for Experiment 1 (FIG. 18A), Experiment 2 (FIG. 18B), Experiment 3 (FIG. 18C), and Experiment 4 (FIG. 18D).

FIGS. 19A–D: Graphs of $q_{O2}$ versus % CFC in the bioreactor for Experiment 1 (FIG. 19A) (y=$1.73 \times 10^{-8}$x+ $3.98 \times 10^{-8}$; $r^2$=0.87), Experiment 2 (FIG. 19B) (y=$5.37 \times 10^{-7}$x+$4.5 \times 10^{-8}$; $r^2$=0.66), Experiment 3 (FIG. 19C) (y=$5.5 \times 10^{-7}$x+$5.96 \times 10^{-8}$; $r^2$=0.8) and Experiment 4 (FIG. 19D) (y=$6.12 \times 10^{-7}$x+$3.7 \times 10^{-8}$; $r^2$=0.86).

DETAILED DESCRIPTION OF THE PRESENTLY PREFERRED EMBODIMENTS

A very small population of totipotent stem cells proliferate and differentiate to produce all blood-cell lineages in the body. Less primitive pluripotent stem cells may differentiate only into a subset of lineages. The intermediate-stage cells that are committed to specific lineages, but are still capable of significant proliferation, are known as progenitor cells. Colony-forming cell assays are the most common type of in vitro assays for progenitor cells, and progenitor cells are also referred to as colony-forming cells (CFC). The final functional cells of each lineage are termed mature blood cells. The mature blood cells include lymphocytes, erythrocytes, neutrophils, macrophages, dendritic cells, and platelets. The mature cells and all of the precursors of mature blood cells (including all of the stem and progenitor cell populations) are termed hematopoietic cells.

In the method of the invention, a reference culture of hematopoietic cells is cultured under selected conditions. Methods of culturing hematopoietic cells and the conditions that affect such cultures are well known. See McAdams et al., Trends Biotechnol., 14, 341–349 (1996) for a review of these methods and conditions. Such conditions include the source of the cells, inoculum density, identity of cytokines used, and physicochemical conditions. The selected conditions are a set of conditions selected for a particular culture which are effective, preferably optimal, for the growth of the hematopoietic cell culture as a whole, or of a particular type of hematopoietic cell. Such effective and optimal conditions are known in the art or can be determined empirically. Making such determinations is within the skill in the art.

There are three main sources of hematopoietic cells for use in the methods of the invention. These are bone marrow (BM), umbilical cord blood (CB) and peripheral blood (PB). While BM has been the traditional source of hematopoietic cells for transplantation therapies, other blood cell sources are becoming more popular. Mobilized PB progenitor cell transplants have proved effective, and it is likely that mobilized PB mononuclear cells (MNC) will replace BM MNC as the preferred source of hematopoietic cells for transplantation (Korbling and Champlin, Stem Cells, 14, 185–195 (1996)). CB is both readily available and easily collected. CB stem cells are thought to be more immature than those found in adults. This attribute makes CB stem cells a potential target for the correction of genetic blood diseases (Clapp and Williams, Stem Cells, 13, 613–621 (1995)).

Methods of collecting BM, CB, and PB are well known in the art. See, e.g., McAdams et al., Trends Biotechnol., 14, 341–349 (1996). Briefly, BM is collected under general anesthesia by multiple needle aspirations to the sternum and/or pelvis. CB is obtained non-invasively from the umbilical cord of newborn infants. BM and CB are often processed by centrifugation over a Ficoll-Histopaque density gradient to deplete the sample of erythrocytes. BM and CB can be cultured without this processing, but high red blood cell content can make visual observation of culture growth quite difficult. PB cells are generally obtained after stem cell mobilization, which is achieved by the administration of one or more of several chemotherapeutic drugs and/or growth factors (often granulocyte colony stimulating factor (G-CSF)) to the patient. By an as yet unknown mechanism, these drugs and factors cause a large number of stem and progenitor cells to proliferate and/or exit the BM and enter the peripheral circulation. Nucleated cells are then collected from the patients using a blood-processing machine; this collection process is known as peripheral blood apheresis.

Purified CD34$^+$ cells can be used in the cultures of the invention. CD34 is a surface glycoprotein of unknown function that is found on approximately 1% (0.1–10%) of collected hematopoietic mononuclear cells (MNCs). It is present on all of the most primitive cells, from the quiescent stem cells to the highly proliferative progenitor cells. As nearly all of the proliferative potential initially present in hematopoietic cell cultures is represented by the CD34$^+$ cells, a number of methods have been developed for their selection. All of these methods rely upon the use of an antibody which recognizes the CD34 antigen and subsequent recovery of the cell-antibody complex. For instance, the cells may be treated with a hapten-conjugated anti-CD34 antibody, and then collected by attachment to anti-hapten antibodies coupled to adsorption columns or magnetic beads. These methods will provide cell populations enriched in CD34$^+$ cells, but the degree of purity will vary depending on the method used. For applications which require extremely high purity (>95%) CD34$^+$ cells, fluorescence-activated cell sorting (FACS) is recommended. See de Wynter et al., Stem Cells, 13, 524–532 (1995) for a review of CD34$^+$ isolation techniques. See also Papadimitriou et al., J. Hematotherapy, 4, 539–544 (1995); Winslow et al., Bone Marrow Transplant, 14, 265–271 (1994). When compared with MNCs, cultures initiated with CD34+ cells have much greater expansion potential. However, CD34+ selection is often expensive and often results in significant cell loss. CD34+ cell populations also lack accessory cells, such as macrophages, that may provide cytokines and other stimulatory factors in MNC cultures.

The expansion potential of different sources of hematopoietic cells, and even of different samples of the same type of cells, is usually subject to large variations of up to several orders of magnitude. CB has greater expansion potential than the other sources, while PB has the greatest variation owing to the wide variety of mobilization regimens and disease states of the patients from whom samples are taken. Also, as noted above, CD34+ cells have greater expansion potential than MNCs. The kinetics of cell expansion also differ greatly between different samples of the same types of cells.

The invention will allow those skilled in the art to estimate the progenitor cell (CFC) content in cultures with differing expansion kinetics and potential. However, the cells in the reference and experimental cultures must be from the same source (e.g., CB), must be from similar samples (e.g., samples from similar donors (age-matched, same disease states, same treatments)) or samples which have similar CD34+ contents, and must be processed in the same way once removed from the donor. For instance, if PB is the source of the cells, the reference culture must employ PB cells from a patient with the same disease state as the source of the cells for the experimental culture and the same mobilization regimen must be used, or the reference and experimental cultures must be initiated from samples having similar contents of CD34+ cells. As another example, if purified CD34+ cells are used in the experimental culture, purified CD34+ cells must also be used in the reference culture. Also, if frozen samples of cells are used in the experimental culture, then frozen samples must be used in the reference culture.

The inoculum density refers to the quantity of MNCs or CD34+ cells per unit volume in the cell population used to initiate the cultures. Inoculum densities based on CD34+ cells can be, and are preferably, used even when the cells are not purified CD34+ cells. The use of CD34+ inoculum densities is preferable because CD34+ cells are much more proliferative than are more mature C34− cells. It is, therefore, expected that standardization with respect to CD34+ cell content will give greater reproducibility and more reliable results.

Methods of determining the number of MNCs and CD34+ cells present in a sample are well known in the art. Preferably, the MNCs are counted using a Coulter Counter or similar apparatus (see Example 1). Preferably, the percentage CD34+ cells is determined by flow cytometry.

For static cultures, the inoculum density of MNCs should not be below $5 \times 10^4$ cells/ml or above $5 \times 10^5$ cells/ml. For CD34+ cell cultures, the inoculum density should not be below $2 \times 10^4$ cells/ml and should not exceed $5 \times 10^4$ cells/ml. Higher inoculum densities will deplete key nutrients too quickly, necessitating frequent feeding of the cultures, and lower densities will not provide reproducible cell expansion. In general, within the limits given above, lower density cultures will exhibit a greater expansion of total cells and progenitor cells than higher density cultures. However, if a large number of cells are required, higher density cultures are recommended since higher densities produce greater total cells and CFCs.

For stirred cultures carried out in spinner flasks utilizing a serum-containing medium, the inoculum density for MNCs should be no lower than $2 \times 10^5$ cells/ml. For serum-free cultures, the inoculum density should be no lower than $3 \times 10^5$ cells/ml. For CD34+ cultures, the inoculum density should be no lower than $5 \times 10^4$ cells/ml for either type of medium. MNC cultures as high as $1.5 \times 10^6$ cells/ml have been initiated with good results. Inoculum densities for CD34+ cultures should not exceed $1.2 \times 10^5$ cells/ml. A good intermediate inoculum density for both serum-containing and serum-free cultures is $5 \times 10^5$ cells/ml for MNC cultures and $7.5 \times 10^4$ cells/ml for CD34+ cultures.

For stirred cultures carried out in a bioreactor, the optimal inoculum density ranges have not yet been established. However, they are expected to be similar to those for spinner flask cultures. For example, MNC cultures in bioreactors in serum-containing medium have been initiated with good results using inoculum densities of $0.2$–$1.7 \times 10^6$ cells/ml. As used herein, "bioreactor" means any culture vessel which provides a full-instrumented, well-controlled, closed and reproducible culture environment.

Cytokines must be included in hematopoietic cell cultures to obtain proliferation and differentiation of hematopoietic cells. Suitable cytokines, their properties, and guidelines for their use in hematopoietic cultures are known in the art. See Sui et al., *Proc. Natl. Acad. Sci.* (*USA*), 92, 2859–2863 (1995); Farese et al., *Blood*, 87, 581–591 (1996); Gore et al., *Exp. Hematol.*, 23, 413–421 (1995); Mayani et al., *Blood*, 81, 3252–3258 (1993); Sonoda et al., *Proc. Natl. Acad. Sci.* (*USA*), 85, 4360–4364 (1988); Tanaka et al., *Blood*, 86, 73–79 (1995); Massague and Pandiella, *Ann. Rev. Biochem.*, 62, 515–541 (1993); Nathan and Sporn, *J. Cell. Biol.*, 113, 981–986 (1991); Nicola, *Ann. Rev. Biochem.*, 58, 45–77 (1989). Also, it is expected that new cytokines will be discovered or developed which can be used in the methods of the invention. Effective and optimal concentrations of cytokines for use in hematopoietic cultures are known in the art or can be determined empirically, and making such determinations is within the skill in the art. Additionally, by appropriate choice of the cytokines used in the culture, broad expansion across multiple hematopoietic lineages or expansion of a specific lineage of cells can be obtained. The chosen cytokine(s) should produce an increase in total cells whether multiple lineages or a single lineage is expanded.

Cytokines can be classified into three groups:

i. a group acting on primitive hematopoietic cells (e.g. stem cell factor, Flt3 ligand);

ii. a group acting on a wide array of progenitor cells (e.g. interleukin-3, interleukin-6, granulocyte-macrophage colony stimulating factor, PIXY321); and iii. a group acting on more mature, lineage-restricted cells (e.g. granulocyte colony stimulating factor, macrophage colony stimulating factor, erythropoietin, thrombopoietin).

Depending on the desired culture product, a combination of these cytokines is typically utilized. Most expansion protocols use a combination with at least one cytokine from each of groups i and ii and perhaps one cytokine from group iii. For instance, a protocol for granulocyte production might utilize a combination of stem cell factor, interleukin-3, interleukin-6, and granulocyte colony stimulating factor.

The above list of cytokines is by no means exhaustive. There are several additional cytokines that can be used. See, e.g., McAdams et al., *Trends Biotechnol.*, 14, 341–359 (1996); McKenna et al., *Blood*, 86, 3413–3420 (1995); and Debili et al., *Blood*, 86, 2516–2525 (1995). Also, "designer" cytokines have been developed which combine the active regions of two cytokines or mimic the binding domain of the cytokine receptor ligand and which have enhanced or novel activities. See, e.g., McAdams et al., *Trends Biotechnol.*, 14, 341–359 (1996). As noted above, it is expected that new cytokines will be discovered or developed which can be used in the methods of the invention.

The physicochemical conditions that affect hematopoietic cell cultures are well known and include the culture medium, pH, incubation conditions (e.g., atmosphere and temperature), type of culture vessel, feeding schedules, biocompatibility of tissue culture materials, culture system (e.g., stirred versus static), etc. For a review of these physicochemical conditions and their effects on hematopoietic cell cultures, see McAdams, et al., *Trends Biotechnol.*, 14, 341–349 (1996). Some of these conditions will be discussed briefly.

Either serum-containing or serum-free medium can be used in hematopoietic cultures. Serum-containing medium generally gives higher progenitor cell and total cell expansion. However, if a more defined medium is desired (e.g., for clinical applications), acceptable expansion can be obtained using serum-free medium. Also, serum-containing medium favors the expansion and maturation of the granulocyte and macrophage lineages, while serum-free medium promotes greater expansion of the erythroid and megakaryocyte lineages. Equilibrating the medium with the incubation atmosphere and temperature is recommended prior to adding the cells to the medium.

The biocompatibility of materials is an important issue in hematopoeitic cultures. Tissue culture treated polystyrene, commonly utilized in the construction of well plates and T-flasks, is biocompatible with hematopoietic cells. However, other materials commonly used for the construction of culture devices for animal cells may not be compatible with hematopoietic cells. Silicone, glass and polycarbonate are a few of the materials which adversely affect hematopoietic culture performance, as identified in a recent publication. LaIuppa, *J. Biomed. Mat. Res.*, 36, 347–359 (1997). See also, McAdams et al., *Trends Biotechnol.*, 14, 341–349 (1996). When designing culture systems, the performance of hematopoietic cells on a chosen material should be evaluated before use of the material in cultures. Material compatibility is especially important if the culture is carried out in serum-free medium; serum can partially protect hematopoietic cells from the negative effects of some materials.

Oxygen tension plays a significant role in hematopoietic culture performance. The oxygen tension of the gas in the headspace of the culture is typically 5–20%. Studies suggest that culturing at a reduced oxygen tension (5%) may be beneficial for progenitor cell expansion. LaIuppa et al., *Exp. Hematol.*, 26, 835–843 (1998); McAdams, et al., *Trends Biotechnol.*, 14, 341–359 (1996); Koller et al., *Ann. New York Acad. Sci.*, 665, 105–116 (1992); Koller et al., *Exp. Hematol.*, 20, 264–270 (1992); Koller et al., *Blood*, 80, 403–411 (1992).

Suitable feeding protocols are known in the art or can be determined empirically, and making such determinations is within the skill in the art. In general, the higher the inoculum density and the higher the cell density present in a culture, the more often feeding of a hematopoietic culture (static or stirred) will be required.

One protocol for feeding stirred or static cultures is replacing 50% of the culture medium every other day beginning on day 4 of culture (referred to herein as "FP1"). FP1 results in very high cell densities and has been found to give good levels of expansion of total cells and CFC (progenitor cells) (see Examples 1 and 2). However, FP1 has also been found to limit the expansion of total cells, particularly post-progenitor cells (see Example 2).

As a consequence, another feeding protocol (referred to herein as "FP2") was developed which provides for greater expansion of total cells (see Example 2). In FP2, the cell density of the culture is adjusted every other day or, preferably, every day to $1.5–2.0 \times 10^6$ cells/ml. To make this adjustment of the cell density, a portion of the spent culture medium containing cells is replaced with fresh culture medium. The same effect can be obtained by simply diluting the cell culture every other day or, preferably, every day using fresh medium (with no removal of spent medium or cells). To do so, a sufficiently large culture vessel or multiple culture vessels (with the cell mixture proportionally distributed between them) with adequate control of pH and oxygen tension must be used to accomodate the greater volume. Further, the total cell density could be measured on-line using a cell density probe, and medium addition (and the removal of cells and spent medium, if necessary) could be carried out continuously as part of an automated system. Using FP2, expansion of total cells and CFC (progenitor cells) is substantially increased compared to FP1 (see Example 2, Table 1). Also, expansion of post-progenitor cells was not inhibited as it was with FP1.

It should be noted that the combination of certain feeding protocols and growth factors can stimulate a culture to contain a large percentage of monocytes, and monocytes have a greater $q_{gluc}$ and $q_{lac}$ than do other mature cells, although still less than CFCs. If the percentage of monocytes is high enough, the correlation of maximum % CFC with maximum $q_{gluc}$ and $q_{lac}$ does not hold. Accordingly, feeding protocols which stimulate the generation of large percentages of metabolically active monocytes should be avoided if it is desired to rely on glucose consumption or lactate production for determination of CFC content of a hematopoietic cell culture. This is not a major limitation, however, because large numbers of monocytes are not normally desired for transplantation therapies. Moreover, it appears that monocytes do not consume large amounts of oxygen, so the correlation between % CFC and $q_{o2}$ can be used to estimate CFC content in cultures containing monocytes (see Example 2).

To employ the methods of the invention, the reference and experimental cultures must be cultured under "essentially the same" conditions. "Essentially the same" means: (1) that the source of the cells is the same for the reference and experimental cultures; (2) that the cells in the reference and experimental cultures are from similar samples; (3) that cells are processed in the same manner; (4) that the inoculum densities of the reference and experimental cultures are similar; (5) that the same cytokines are used in the reference and experimental cultures; (6) the same feeding protocol is used; and (7) that the initial physicochemical conditions of the reference and experimental cultures are the same. Quantitative measurements (e.g., many of the physicochemical conditions) are normally subject to measurement errors. Thus, "same" means that such quantitative measurements are the same subject to normal measurement errors. As noted above, the inoculum densities need only be "similar." For instance, if mononuclear cells are used, the CD34$^+$ cell contents of the reference and experimental cultures may differ by about ±1% (by contrast, the normal measurement error for CD34$^+$ cells is about ±0.1%). For example, if the experimental culture contains 5% CD34$^+$ cells, the reference culture should contain 4–6% CD34$^+$ cells.

The reference culture can be performed at any time prior to performing the experimental culture. However, the reference culture is preferably repeated whenever a reagent or equipment is changed (e.g., a new supplier of a reagent, a new batch or lot of a particular reagent, a new incubator).

Also, several reference cultures can be performed covering normal operating conditions. For instance, reference cultures can be performed employing the different culture conditions usually used in a particular laboratory or the different culture conditions usually used in a culture intended for a particular end use of the cultured cells. Also, several reference cultures can be performed employing the usual range of $CD34^+$ cells encountered in a particular source of cells.

The invention provides a method of determining the content of progenitor cells in a hematopoietic cell culture. As used herein, "content" refers to the relative number of progenitor cells in the culture and to the absolute number of progenitor cells in the culture. For instance, % CFC or total CFC in a hematopoietic cell culture can be determined. Also, the time at which progenitor cells are at a maximum concentration can be determined.

The content of progenitor cells in a hematopoietic cell culture is determined by measuring one or more metabolic parameters. "Metabolic parameter" is used herein to mean any measure of the metabolic activity of the cells. "Metabolic parameters" which can be used to determine the progenitor cell content of hematopoietic cell cultures include glucose consumption, lactate production, oxygen consumption, pyruvate consumption, ammonia production, carbon dioxide production, and production or consumption of one or more amino acids.

Devices and methods for measuring glucose consumption, oxygen consumption, and lactate production of cultures are well known. Suitable devices for making such measurements are available commercially from, e.g., Yellow Springs Instruments, Kodak, Ingold and Instrumentation Laboratories. See also Examples 1 and 2.

Devices and methods for measuring pyruvate consumption, ammonia production, carbon dioxide production, and production or consumption of amino acids are also well known. For instance, amino acid consumption or production can be measured by high pressure liquid chromatography (devices available commercially from Waters or Hewlett-Packard), ammonia production can be measured using an ion-specifc electrode (available commercially from Orion), pyruvate consumption can be measured using an enzymatic assay (device available from Sigma), and carbon dioxide production can be measured using a blood gas analyzer (devices available from Instrumentation Laboratories or Corning).

The one or more metabolic parameters must be measured in the reference culture at two or more selected times. Preferably five measurements at five selected times, more preferably eight measurements at eight selected times, will be made. Even more preferably, measurements will be made once a day every day for ten or more days. Most preferably, measurements will be made continuously.

The one or more metabolic parameters must also be measured at one or more selected times for the experimental culture. At least one measurement should be made early in the culture (preferably at 24–48 hours) to confirm that the culture is performing as expected based on the performance of the reference culture. If not, corrective action can be taken or another source of cells for the end use can be found. Several additional measurements should be made during the experimental culture to confirm that the maximum or desired number of progenitor cells is present in the culture prior to harvesting. In a preferred embodiment, the one or more metabolic parameters is(are) monitored daily. Even more preferably, the experimental culture is monitored continuously, and the measurements are fed to a computer which calculates the content of the progenitor cells. With daily or continuous monitoring, the best time to harvest the culture can be easily identified. Also, any problems with the culture can be identified at the earliest possible moment.

The number of progenitor cells (CFC) in the reference culture must be determined. Assays for CFC (as a group or specific types) are well known in the art (see the Background section and Example 1). The total number of nucleated cells used to initiate the CFC assay is also determined by methods well known in the art, preferably using a Coulter Counter or other similar apparatus (see Example 1). Using these two measurements, the % CFC can be calculated at each selected time.

The density or concentration of nucleated cells in the reference culture is also measured at each of the selected times. Suitable methods of doing so are the same as for measuring nucleated cells for the CFC assays. For instance, the density of nucleated cells can be measured using a Coulter Counter or other similar apparatus (see Example 1). When continuous measurements are employed, cell density or concentration can measured using an optical probe. Suitable optical probes are available from Aquasent, Ingold, Monitek and Wedgewood.

Finally, the measurements of the one or more metabolic parameters for the experimental culture are compared to those measured for the reference culture to determine the content of progenitor cells in the experimental culture at one or more selected times. The comparison can be made graphically or by use of mathematical equations setting forth the relationship between the measured metabolic parameter (s) and the content of progenitor cells.

For example, the total glucose consumed, total oxygen consumed, or the total lactate produced per ml by a reference culture is measured once a day every day for ten days. The density of nucleated cells and % CFC of the reference culture are also determined at each of these times. The measured cell density, % CFC, and glucose consumption, oxygen consumption or lactate production of the reference culture are used to calculate $q_{gluc}$, $q_{o2}$ or $q_{lac}$, and to determine $\alpha_{gluc}$ and $\beta_{gluc}$, $\alpha_{o2}$ and $\beta_{o2}$ or $\alpha_{lac}$ and $\beta_{lac}$ using the equations set forth in Examples 1 and 2 below. The values of $\alpha_{gluc}$ and $\beta_{gluc}$, $\alpha_{o2}$ and $\beta_{o2}$, or $\alpha_{lac}$ and $\beta_{lac}$ can be determined as described in Examples 1 and 2 employing a graph of $q_{gluc}$, $q_{o2}$ or $q_{lac}$ versus % CFC. Alternatively, the values of $\alpha_{gluc}$ and $\beta_{gluc}$, $\alpha_{o2}$ and $\beta_{o2}$ or $\alpha_{lac}$ and $\beta_{lac}$ can be determined using linear regression analysis employing least squares fit, preferably by computer, to calculate the values of $\alpha_{gluc}$ and $\beta_{gluc}$, $\alpha_{o2}$ and $\beta_{o2}$ or $\alpha_{lac}$ and $\beta_{lac}$ from equation (9), (21) or (6), respectively.

Then, the density of nucleated cells of, and total glucose consumed, total oxygen consumed or the total lactate produced per ml by, an experimental culture are measured. These measurements and the values of $\alpha_{gluc}$ and $\beta_{gluc}$, $\alpha_{o2}$ and $\beta_{o2}$ or $\alpha_{lac}$ and $\beta_{lac}$ for the reference culture are used to calculate the % CFC in the experimental culture at the one or more selected times using equation (9), (21) or (6), respectively, set forth in Examples 1 and 2 below. As described in Examples 1 and 2, the % CFC reaches a maximum and then declines. If it is desired to harvest the experimental culture at the time of maximum % CFC, measurements of the glucose consumption, oxygen consumption, or lactate production should begin early in culture and continue until the maximum % CFC is achieved. Of course, as noted above, continuous monitoring of the experimental culture will give the time of maximum % CFC most precisely.

Alternatively, the measured glucose consumption, oxygen consumption or lactate production of the experimental culture is used to calculate $Q_{gluc}$, $Q_{O2}$ or $Q_{lac}$, the concentration of nucleated cells ($X_i$) in the experimental culture is measured, and the measured $X_i$ and the calculated $Q_{gluc}$, $Q_{O2}$ or $Q_{lac}$ for the experimental culture and the values of $\alpha_{gluc}$ and $\beta_{gluc}$, $\alpha_{O2}$ and $\beta_{O2}$ or $\alpha_{lac}$ and $\beta_{lac}$ for the reference culture are used to calculate the total number of CFC at the selected time(s) for the experimental culture. These calculations are made using equations (7), (22) or (4), respectively, set forth in Examples 1 and 2. As with % CFC, if it is desired to harvest the experimental culture at the time of maximum total CFC, measurements of the glucose consumption, oxygen consumption or lactate production should begin early in culture and continue until the maximum total CFC is achieved. Of course, continuous monitoring of the experimental culture will give the time of maximum total CFC most precisely.

Monitoring glucose consumption, oxygen consumption or lactate production is also useful in determining when cells have exited from quiescence. This exit is evidenced by a rapid increase in $q_{gluc}$, $q_{O2}$, or $q_{lac}$, indicating the beginning of rapid proliferation. This information could be useful for determining when to introduce genetic material to hematopoietic cells for the purpose of gene therapy, since most gene therapy transfection protocols require that the host cells be in a cycling state.

EXAMPLES

Example 1

In this example, the correlation of glucose consumption and lactate production with colony-forming cell content in hematopoietic cell cultures was investigated.

A. Media and Reagents

Media—Human long term medium (HLTM), which was used as the standard serum-containing medium, consists of McCoy's 5A basal medium (Sigma, St. Louis, Mo.), 12.5% heat inactivated horse serum (Sigma), 12.5% fetal bovine serum (Hyclone, Logan, Utah), 1 mM sodium pyruvate (Sigma), 1% MEM vitamin solution (Irvine Scientific, Irvine, Calif.), 1% MEM amino acid solution (Irvine Scientific), 1% MEM non-essential amino acid solution (Irvine Scientific), $10^{-4}$ M monothioglycerol (Sigma), 2 mM L-glutamine (Sigma), and 50 µg/ml gentamycin sulfate (Gibco, Grand Island, N.Y.). XVIVO-20 (BioWhittaker, Walkersville, M.d.), was used as the standard serum-deprived medium.

Cytokines—All cytokines used were purified recombinant human factors. Interleukin-3 (IL-3, Sandoz, East Hanover, N.J.) was used at 5 ng/ml, IL-6 (Sandoz) at 10 ng/ml, stem cell factor (SCF, Amgen, Thousand Oaks, Calif.) at 50 ng/ml, Flt3 ligand (Flt3-l, Immunex, Seattle, WA) at 50 ng/ml, granulocyte-colony stimulating factor (G-CSF, Amgen) at 1.5 ng/ml, granulocyte-macrophage-CSF (GM-CSF, Immunex) at 2 ng/ml, and erythropoietin (Epo, Amgen) at 28 ng/ml in liquid cultures.

B. Cells and Cell Separation Procedures

Patient samples (Response Oncology; Memphis, Tenn.) of peripheral blood (PB) were collected after informed consent under protocols approved by the respective Institutional Review Boards. Apheresis products were collected from cancer patients following stem cell mobilization regimens consisting of treatment with G-CSF with or without chemotherapy. The samples were used as received; density gradient separation of the mononuclear cell (MNC) fraction was not required due to minimal erythrocyte content. Umbilical cord blood (CB) samples were provided by Northwestern University Memorial Hospital (Chicago, Ill.). CB MNC were isolated from the whole sample by density gradient separation on Histopaque (1.077 g/ml, Sigma). Positive selection of CD34 antigen-bearing cells (CFC are contained within the CD34$^+$ cell population) was accomplished by utilizing MiniMACS (Miltenyi Biotech, Inc., Sunnyvale, Calif.) magnetic separation columns following the directions of the manufacturer. The number of nucleated cells was determined on a Coulter Counter Multisizer (Coulter Electronics, Hialeah, Fla.) after treatment with cetrimide solution (90 g cetrimide (hexadecyltrimethylammonium bromide)powder (Sigma), 25 g NaCl (Sigma), 1.1 g. EDTA (Sigma) in 3 L deionized water) to lyse the cells and release the nuclei. The error associated with the preparation and measurement of cell density was estimated to be ±5%.

C. Methylcellulose Colony Assays

The numbers of granulocyte, monocyte/macrophage, erythroid, and mixed-lineage progenitor cells were determined using a methylcellulose colony assay as described previously (Koller et al., *Blood*, 80, 403–411 (1992)), with slight modifications. The 1.1% methylcellulose medium was supplemented with IL-3, IL-6, SCF, GM-CSF, G-CSF, and Epo at the concentrations listed above for liquid culture, with the exception of Epo, which was added at a concentration of 83 ng/ml. Cultures were plated at seeding densities ranging from 2,000 cells/ml to 15,000 cells/ml for fresh and cultured MNC and from 500 cells/ml to 10,000 cells/ml for cultures initiated with CD34$^+$ cells. The inoculum density for methylcellulose culture was determined both by the degree of total cell expansion in the culture and the day of culture since the cloning efficiency drops as the total cell expansion rises. The methylcellulose plating density was, therefore, increased as the culture expanded in an effort to maintain a total of 100–300 CFC per dish. By so doing, the effects of either overplating or underplating the methylcellulose culture that occur when a fixed seeding density is used at all time points are avoided. The methylcellulose cultures were incubated for 14 days in a humidified atmosphere of 5% $O_2$ and 5% $CO_2$ (balance $N_2$). At the end of the incubation period, colonies of 50 or more cells were enumerated as either CFU-GM (including CFU-G and CFU-M), BFU-E, or CFU-Mix through inspection on a dark field stereomicroscope (Zeiss, Batavia, Ill.). The majority of the cultures did not contain detectable numbers of CFU-Mix, so that CFU-Mix was neglected in the analysis. The error associated with enumerating CFC was estimated using Poisson statistics. From the number of each CFC type counted and the plating density, the percentage of each CFC type or total CFC present in the sample was calculated as $$\% \, CFC = \frac{\text{number of colonies per plate}}{\text{plating density (cells per plate)}}$$

D. Stirred Hematopoietic Culture

Stirred cultures were carried out in 100-ml spinner flasks (Bellco model 1967 with model 1965 agitator assembly) with an agitation rate of 30 RPM (see Collins et al., *Chemical Engineering Progress*, Supplement 1, 57a (1996) and Collins et al., *Biotechnol. Bioeng.*, 59, 534–543 (1998), the disclosures of which are incorporated herein by reference). The spinners were not siliconized prior to use, as this was found to be unnecessary. The cultures were fed every 2 days, beginning at day 4, by pipette removal of one half of the cell suspension, centrifugation at 300 g for 10 minutes, removal of the spent medium, and return of the cells with fresh equilibrated medium to the spinner flask (this feeding protocol is referred to herein as FP1). The spinner flasks were maintained within a humidified incubator at 5% $O_2$ and 5% $CO_2$ (balance $N_2$). Samples containing cells and medium were removed by pipette, and the number of nucleated cells enumerated using a Coulter counter. Medium supernatant samples were frozen at −20° C. and retained for metabolite analysis.

E. Static Hematopoietic Culture

Static cultures were carried out in T-75 flasks (Falcon, Lincoln Park, N.J.) for MNC culture or T-25 flasks (Falcon) for CD34$^+$ cell cultures. Static cultures were maintained in the same manner as stirred cultures.

F. Metabolic Assays and Calculations

Medium supernatant samples were thawed and subsequently centrifuged for 10 minutes at 14,000 RPM using an Eppendorf model 5415C centrifuge to remove any particulates that could potentially foul the membranes of the YSI model 2700 glucose/lactate analyzer (Yellow Springs Instruments, Yellow Springs, Ohio). The analyzer was calibrated after every six samples to enhance the accuracy of the assays. The manufacturer's stated assay precision is ±2%, while the linearity is ±2% between 0–13.9 mmole and ±5% between 13.9–138.9 mmole for glucose and ±2% between 0–5.6 mmole and ±5% between 5.6–29.1 mmole for lactate.

Volumetric glucose consumption and lactate generation rates (Q, μmole/ml/hr) were calculated using the second-order central slope method, as follows. The total glucose consumed or lactate generated was calculated for each time point. For any time point ($t_i$), the first order forward (f, from time $t_i$ to $t_{i+1}$) and backward (b, from time $t_{i-1}$ to $t_i$) slopes of the total consumption or generation curve were calculated by dividing the point-to-point metabolite consumption or generation differences by the point-to-point differences in time. The volumetric rate at time $t_i$ was then calculated by taking a time-distance weighted average of these two slopes:

$$Q_i = \frac{(t_{i+1} - t_i)(\text{slope}_b) + (t_i - t_{i-1})(\text{slope}_f)}{(t_{i+1} - t_{i-1})} \quad (1)$$

Specific metabolic rates (q, pmole/cell/hr) at any time $t_i$ were obtained by dividing the volumetric rate by the nucleated cell density $X_i$ (cells/ml) at time $t_i$:

$$q_i = \frac{Q_i}{X_i} \quad (2)$$

The nucleated cell density does not account for enucleated red blood cells (RBC, final stage erythroid cells do not have a nucleus), which may be present in the culture. This enucleated population was not accounted for because the small number of RBC present at inoculation are typically no longer detectable by day 3 and the formation of enucleated RBC was not generally observed in the cultures (as determined by phenotypic examination).

G. Correlation of Culture CFC Content with Specific Metabolic Rates

In examining the specific glucose consumption rate ($q_{gluc}$) and lactate generation rate ($q_{lac}$) for cultures carried out in spinner flasks, it was observed that both $q_{gluc}$ and $q_{lac}$ increased from time zero until a maximum was attained. After that time, both $q_{gluc}$ and $q_{lac}$ fell until they reached a minimum value that was maintained until the end of the culture. A similar decrease (after reaching a maximum) in the fraction of cells in a culture that were CFC (% CFC) suggested a relationship between % CFC and $q_{gluc}$ (or $q_{lac}$). When $q_{gluc}$, $q_{lac}$, and % CFC were plotted vs. time on the same graph, they rose and fell simultaneously (FIG. 1), with the maximum $q_{gluc}$ or $q_{lac}$ observed when the percentage of CFC in culture was the greatest. This suggested that rapidly proliferating CFC have a much greater metabolic demand than more mature cells.

In all experiments conducted, similar trends were observed for glucose consumption and lactate production rates. Lactate data generally displayed less scatter than did glucose data. This was especially true early in cultures inoculated at low cell densities where the error in the glucose assay was of the same order of magnitude as the amount of glucose consumed. For simplicity, most of the remaining discussion is limited to lactate production rates.

Figure 1:
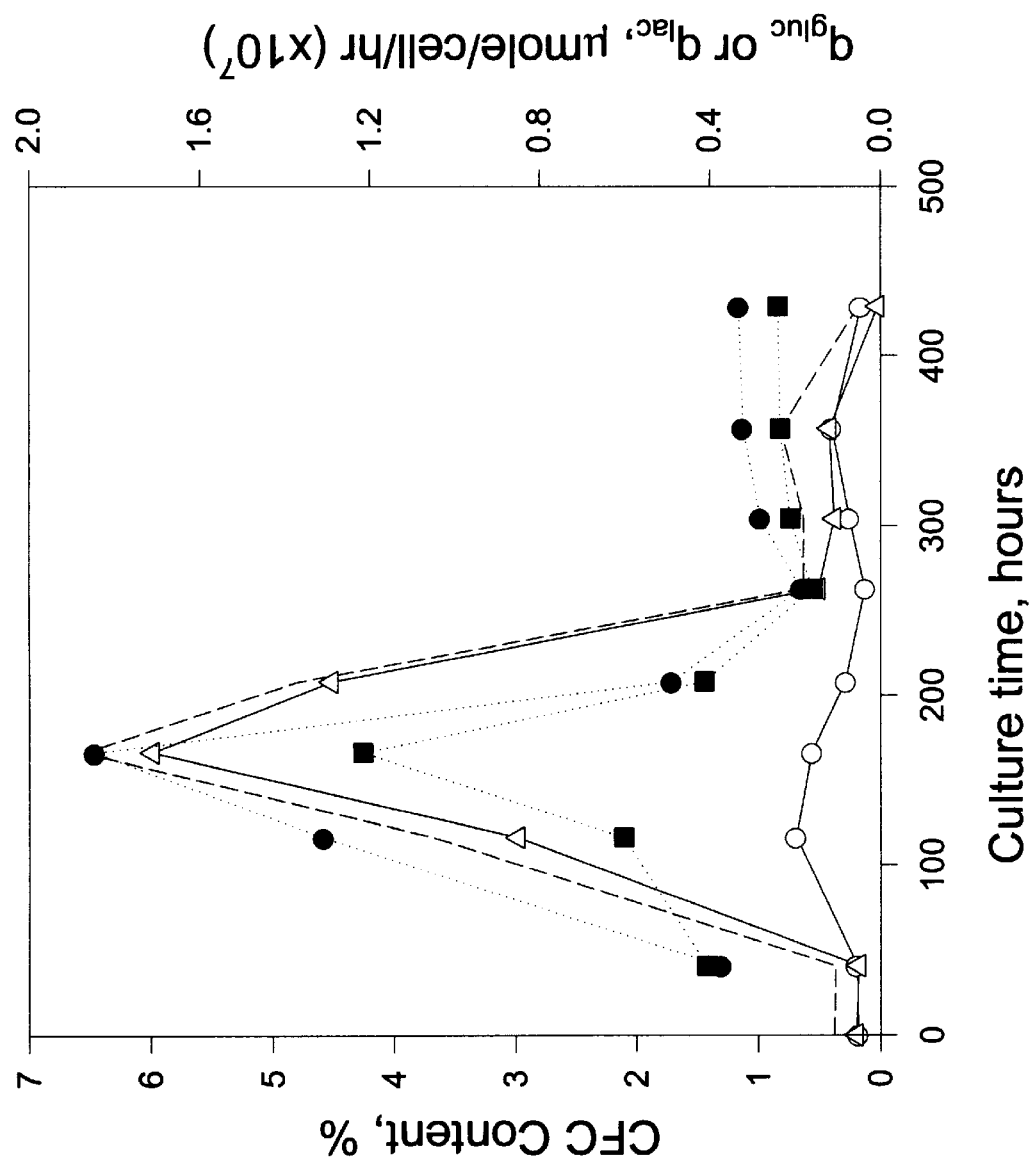
FIG. 1: Time profile for specific glucose consumption rate ($q_{gluc}$) (...■...), specific lactate production rate ($q_{lac}$) (...●...), and the % of cells that are CFU-GM (-○-), BFU-E (-Δ-), and total CFC (CFU-GM+BFU-E) (-----) in a spinner flask. The cord blood (CB) mononuclear cell (MNC) culture was carried out in XVIVO-20 medium with interleukin-3 (IL-3), interleukin-6 (IL-6), stem cell factor (SCF), granulocyte-colony stimulating factor (G-CSF), granulocyte-macrophage colony stimulating factor (GM-CSF), and erythropoietin (Epo) at an inoculum density (ID) of $3.8 \times 10^5$ cells/ml.
Figure 2:
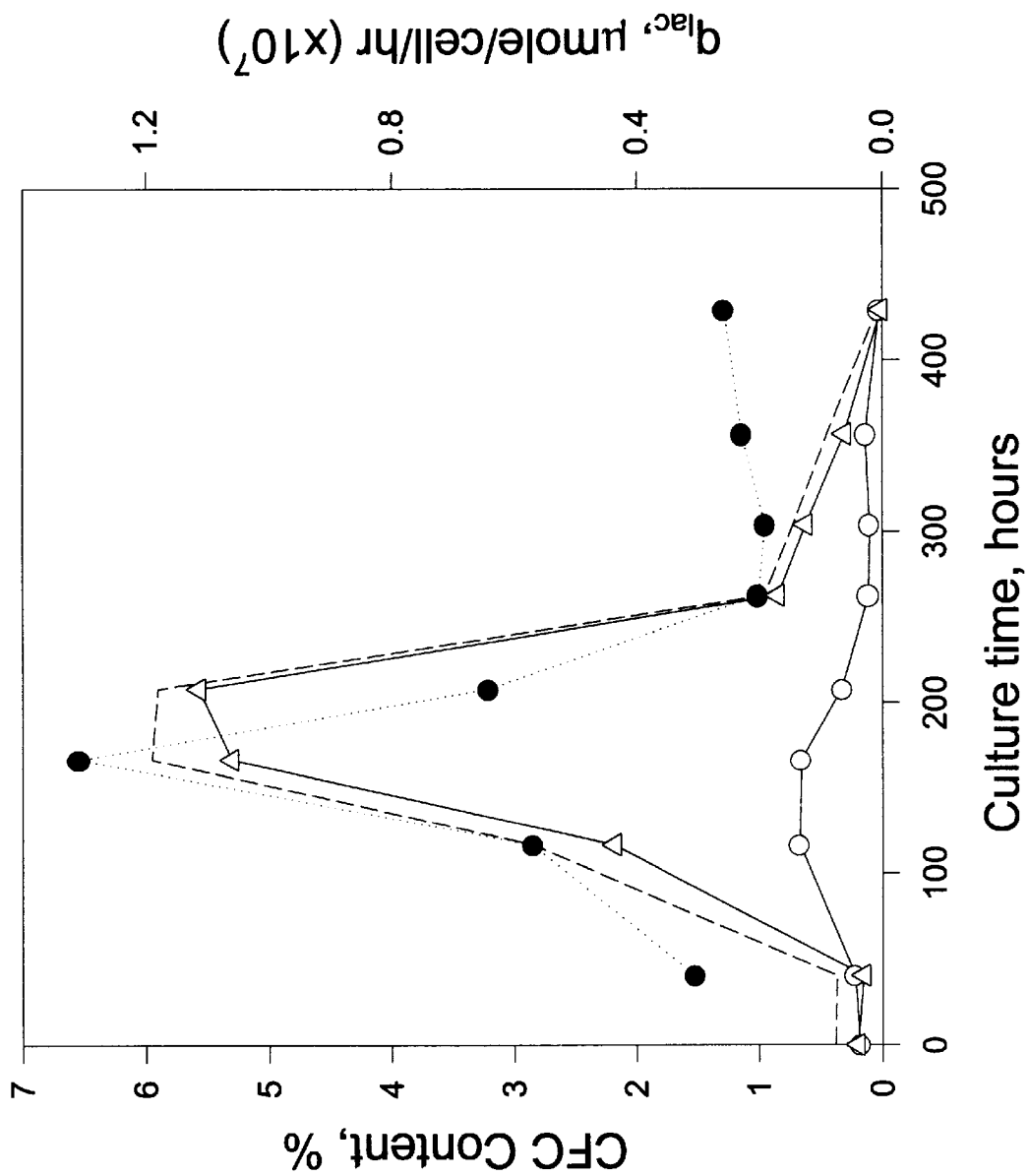
FIG. 2: Time profile for $q_{lac}$ and the % of cells that are CFU-GM, BFU-E and total CFC (CFU-GM+BFU-E) in a T-flask. The sample and culture conditions used and the symbols are the same as in FIG. 1.
Figures 3A, 3B, 3C:
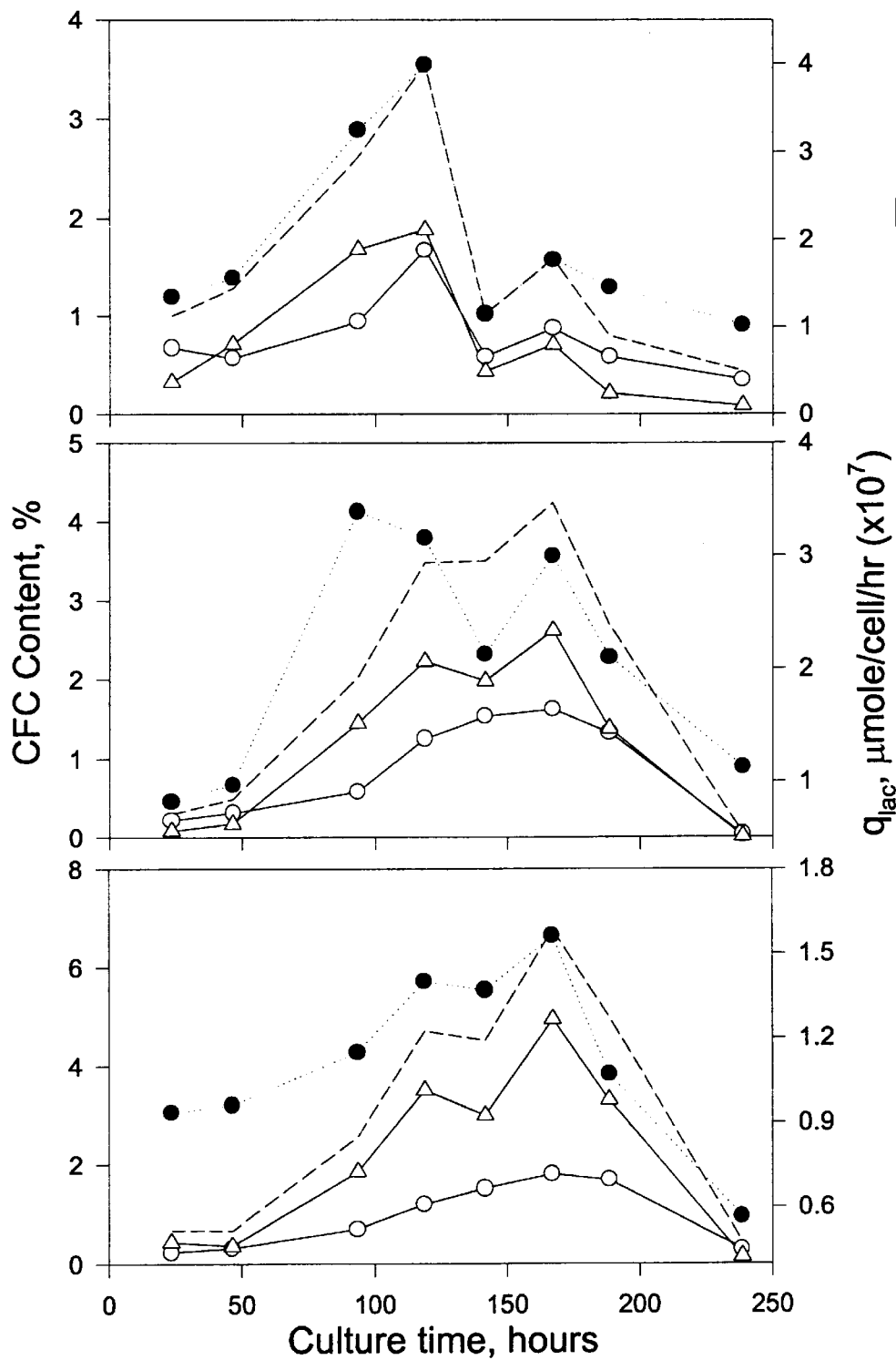
FIGS. 3A–C: Time profiles for $q_{lac}$ and the % of cells that are CFU-GM, BFU-E and total CFC (CFU-GM+BFU-E) in spinner flasks for a single peripheral blood (PB) MNC sample cultured at an ID of 160,000 cells/ml (FIG. 3A), 750,000 cells/ml (FIG. 3B), and 1,260,000 cells/ml (FIG. 3C). All cultures were carried out in human long-term medium (HTLM) with IL-3, IL-6, SCF, G-CSF, GM-CSF, and Epo. The symbols are the same as in FIG. 1.
Figures 4A, 4B:
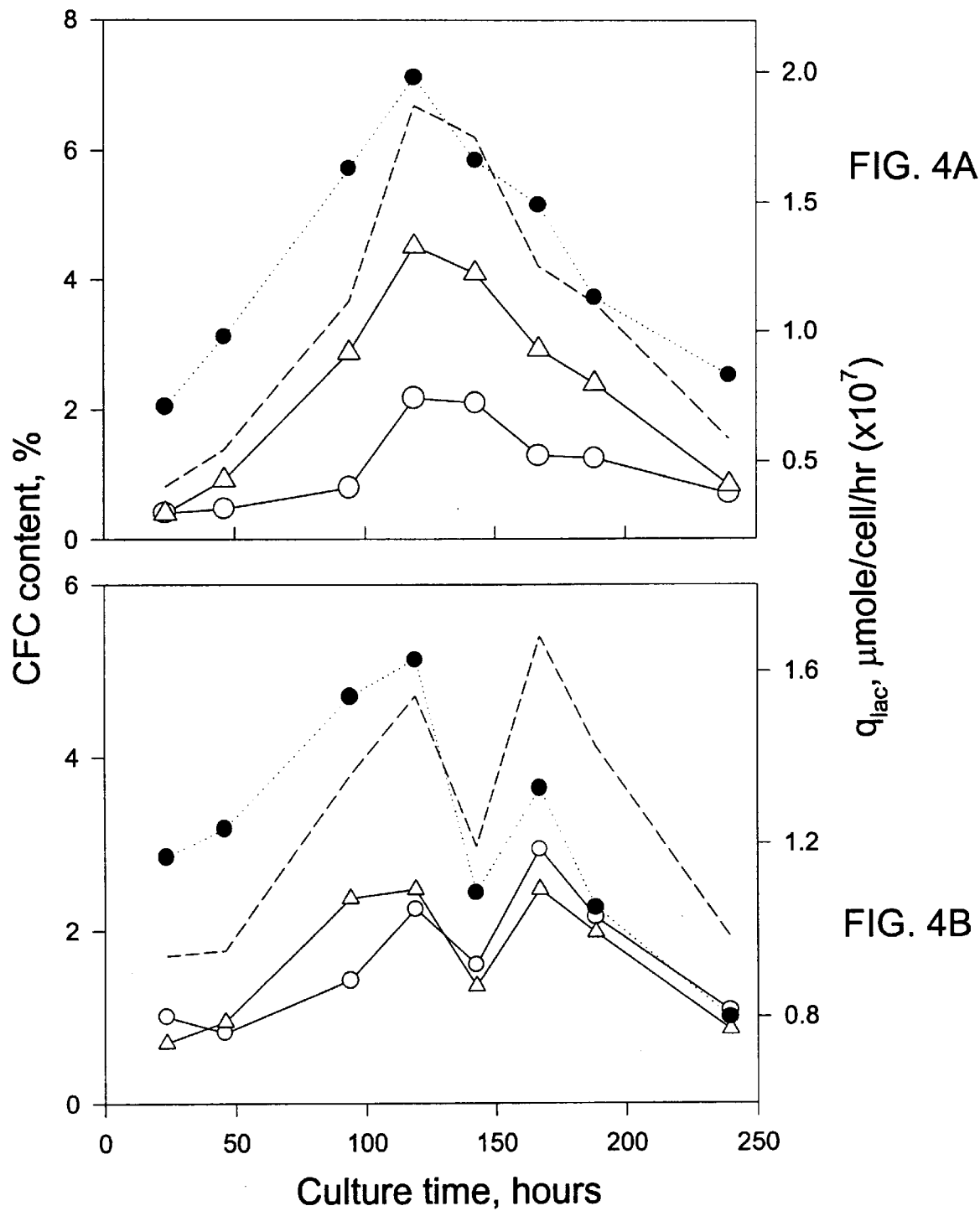
FIGS. 4A–B: Time profiles for $q_{lac}$ and the % of cells that are CFU-GM, BFU-E and total CFC (CFU-GM+BFU-E) in spinner flasks for a single PB MNC sample cultured at an ID of 1,260,000 cells/ml in XVIVO-20 with IL-3, IL-6, SCF, G-CSF and either GM-CSF and Epo (FIG. 4A), or Flt3 ligand (Flt3-l) (FIG. 4B). The symbols are the same as in FIG. 1.
Figures 5A, 5B:
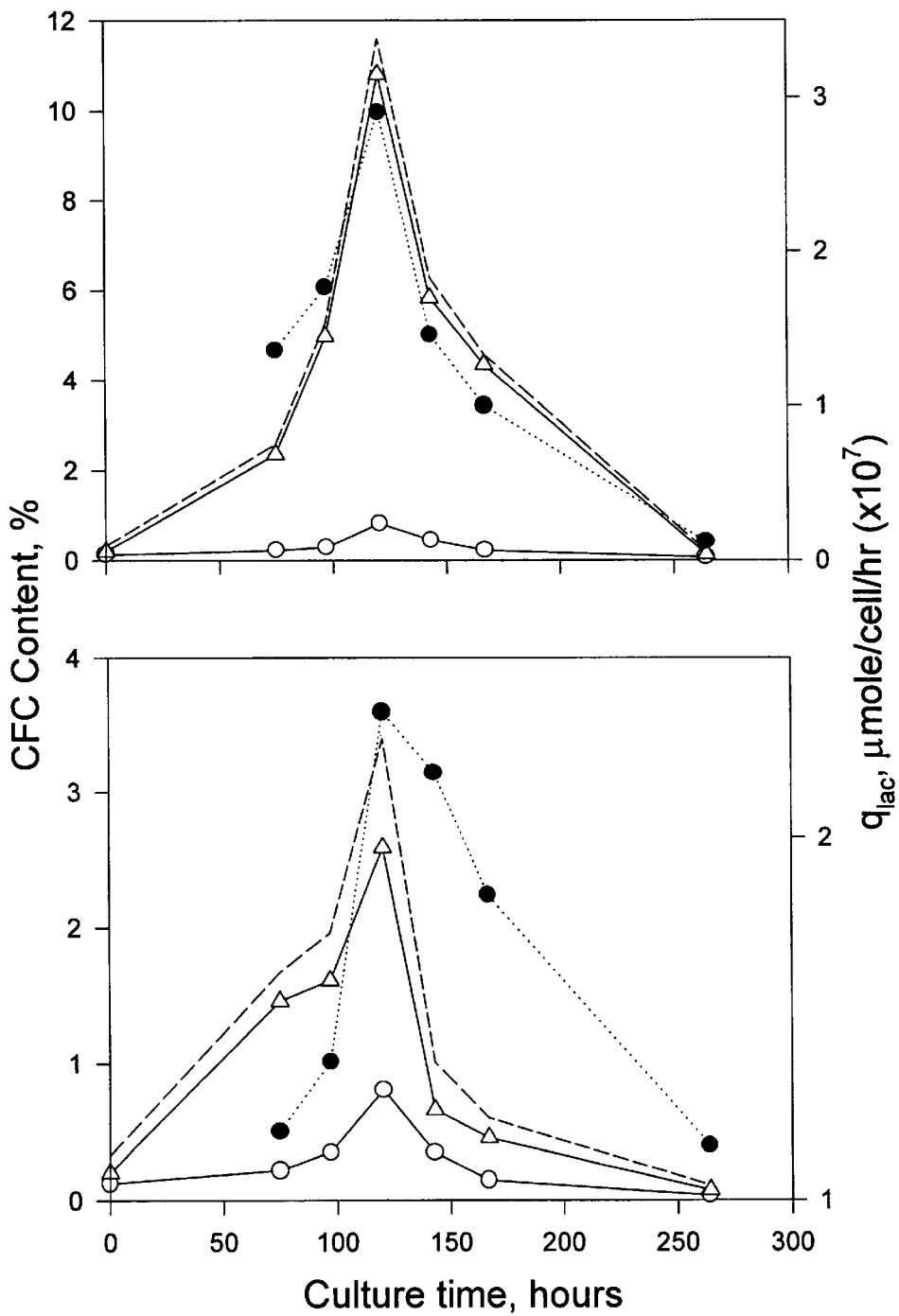
FIGS. 5A–B: Time profiles for $q_{lac}$ and the % of cells that are CFU-GM, BFU-E and total CFC (CFU-GM+BFU-E) in spinner flasks for a single PB MNC sample cultured at an ID of 800,000 cells/ml in XVIVO-20 with IL-3, IL-6, SCF and either Epo (FIG. 5A), or G-CSF (FIG. 5B). The symbols are the same as in FIG. 1.

The data shown in FIG. 1 are for a CB MNC spinner flask culture conducted using XVIVO-20 with IL-3, IL-6, SCF, G-CSF, GM-CSF, and Epo at an inoculum density (ID) of 3.85×10$^5$ cells/ml. However, the relationship between % CFC and $q_{lac}$ is not dependent upon a particular cell source, culture system, medium type, ID, or cytokine combination. To date, this relationship has been observed in more than ten CB MNC, 47 PB MNC, and 18 PB CD34$^+$ cell cultures carried out under a variety of conditions. For example, the correlation between $q_{lac}$ and % CFC shown in FIG. 1 was also evident in a parallel T-flask culture (FIG. 2). For a given cytokine combination, cultures initiated at different ID from the same PB MNC sample exhibited the same interdependence of $q_{lac}$ with % CFC (FIG. 3). The coincidence of $q_{lac}$ and % CFC was also maintained for different cytokine combinations in cultures initiated at the same ID from the same PB MNC sample (FIGS. 4 and 5). The correlation was evident in both serum-containing (FIGS. 3, 6, and results not shown) and serum-free (FIGS. 1, 2, 4, 5, and results not shown) culture media. The shape of the $q_{lac}$ profile is not always the same from culture to culture, but the time of maximum $q_{lac}$ still corresponds to the time of maximum CFC content. The coincidence of maxima in $q_{lac}$ and % CFC also extended to cultures that exhibited local minima and maxima (FIGS. 3 and 4B), although the majority of the cultures did not realize increases in % CFC once the decline from maximum % CFC had begun.

Figures 6A, 6B, 6C:
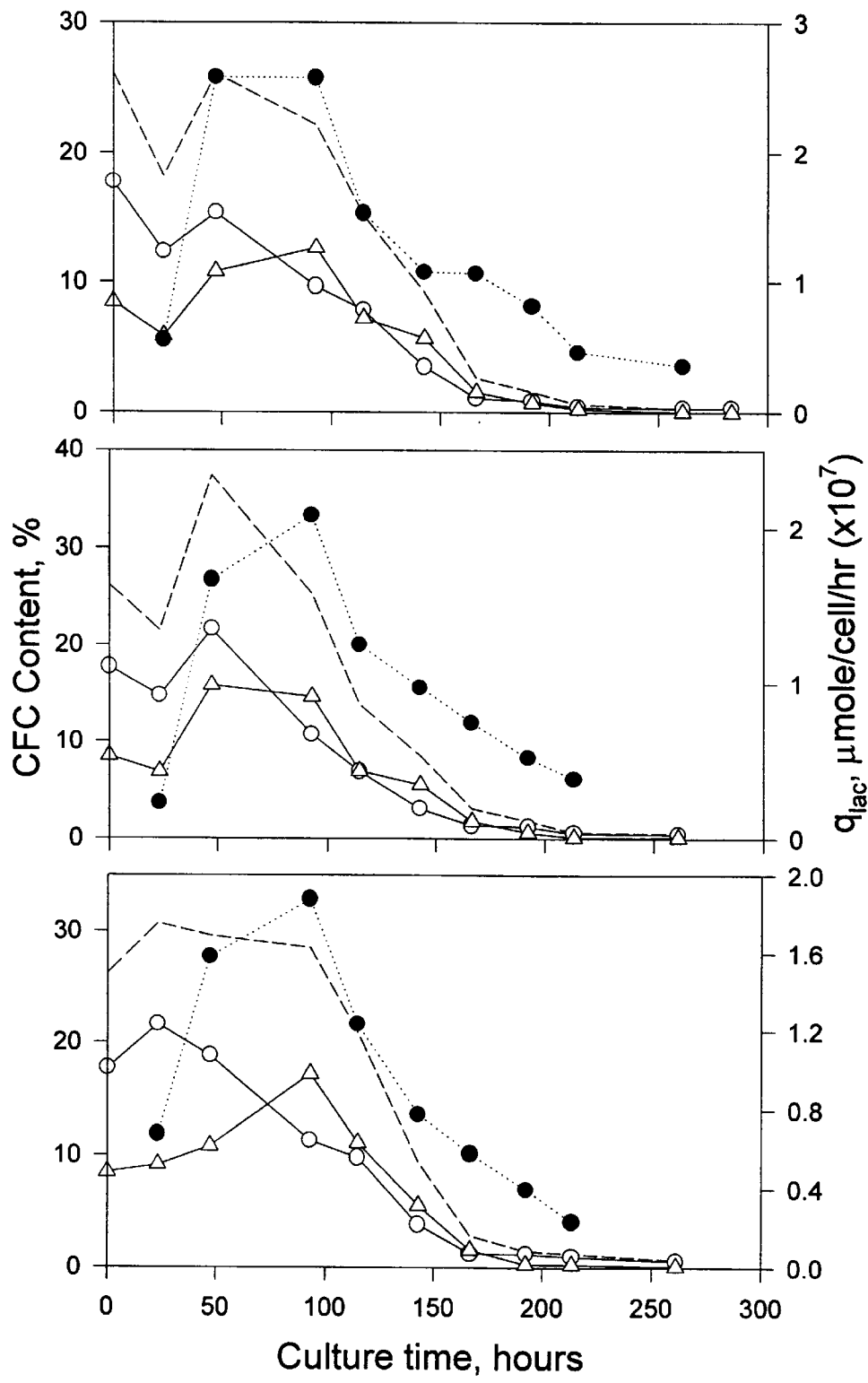
FIGS. 6A–C: Time profiles for $q_{lac}$ and the % of cells that are CFU-GM, BFU-E and total CFC (CFU-GM+BFU-E) in T-flasks for a single PB CD34+ cell sample cultured at an ID of 33,000 cells/ml (FIG. 6A), 82,000 cells/ml (FIG. 6B), and 125,000 cells/ml (FIG. 6C). The cultures were conducted in HLTM with IL-3, IL-6, SCF, G-CSF, GM-CSF, and Epo. The symbols are the same as in FIG. 1.

The maximum CFC content observed in MNC cultures is typically on the order of 10%. The coincidence of maxima for $q_{lac}$ and % CFC held true in cultures with higher CFC content, such as those inoculated with CD34$^+$ cells. In CD34$^+$ cell cultures, the % CFC achieved was much greater (as high as 40%), and the time to maximum % CFC was shorter than in MNC cultures. Despite the differences in initial culture population, maximum CFC content attained, and growth kinetics, the % CFC content was reasonably paralleled by $q_{lac}$ in CD34$^+$ cell cultures with three different ID (FIG. 6). However, it should be noted that the point corresponding to the first calculated $q_{lac}$ value for the three cultures shown in FIG. 6, as well as for most other CD34$^+$ cell cultures, was well below that expected for a culture with such a high % CFC. The low $q_{lac}$ can be attributed to the fact that primitive hematopoietic cells are predominantly in quiescence at the onset of culture (Traycoff et al., *Exp Hematol*, 22, 1264–1272 (1994); Gore et al., *Exp Hematol*, 23, 413–421 (1995)), and would therefore not be expected to demonstrate the high rate of lactate generation associated with rapid proliferation. This period of quiescence applies to MNC cultures as well, but the % CFC present at the beginning of a MNC culture is much lower than that for a CD34$^+$ cell culture.

H. Modeling Cell Metabolism

An exact model of total lactate production would consider each distinct cell type, such that:

$$\frac{\Delta(\text{Lactate})}{\Delta(\text{Time})} = \sum_i (q_{laci} \times n_i) \quad (3)$$

where i represents each individual cell type and $n_i$, the number of cells of type i. However, the large number of hematopoietic cell types makes this model unwieldy. The dramatic decrease in $q_{lac}$ during the differentiation from CFC to post-progenitor cells (for example, see FIG. 5A at 120 hours) suggests that a two-population (CFC and other cells) model provides an adequate description of lactate production, such that:

$$Q_{lac} = \alpha_{lac}[CFC] + \beta_{lac}(X_i - [CFC]) \quad (4)$$

where $\alpha_{lac}$ is the $q_{lac}$ value for a CFC, $\beta_{lac}$ is the $q_{lac}$ value for a non-CFC, $X_i$ is the concentration of total nucleated cells in the culture, and [CFC] is the concentration of total CFC in the culture. Equation (4) can be normalized by dividing both sides by $X_i$. Upon rearrangement, the following relationship is obtained:

$$\frac{Q_{lac}}{X_i} = (\alpha_{lac} - \beta_{lac})\left[CFC\frac{1}{X_i}\right] + \beta_{lac} \quad (5)$$

or $$q_{lac} = (\alpha_{lac} - \beta_{lac})\frac{\% \, CFC}{100} + \beta_{lac} \quad (6)$$

If this two-population model adequately describes the data, a plot of $q_{lac}$ versus the % CFC in a culture will yield a straight line with the y-intercept giving $q_{lac}$ for a non-CFC and the slope yielding the difference between $q_{lac}$ for a CFC and that for a non-CFC.

FIG. 7 shows the linear relationship between $q_{lac}$ and % CFC for a CB MNC culture in HLTM with IL-3, IL-6, SCF, G-CSF, GM-CSF, and Epo. The line though the data points was generated by linear regression. In FIG. 7, the y-intercept $\beta_{lac}$ ($q_{lac}$ for a non-CFC) is $2.5 \times 10^{-8}$ μmole/cell/hr. The calculated $\alpha_{lac}$ for the data in FIG. 7 is $5.3 \times 10^{-6}$ μmole/cell/hr. Since $\alpha_{lac}$ is approximately 200-fold greater than $\beta_{lac}$, this substantiates the hypothesis that the average CFC has a much greater $q_{lac}$ than does a more differentiated cell.

Regression analysis (FIG. 8) was also performed on the data previously presented in time-course form in FIG. 3. As before, a reasonable straight-line relationship was obtained between $q_{lac}$ and % CFC. Again, the calculated $\alpha_{lac}$ is much greater than $\beta_{lac}$ for each plot. The degree of correlation varied for the different cultures, but, in most cases, points that deviate from the regression line are explained by the errors associated with the % CFC and $q_{lac}$ calculations.

As mentioned above, hematopoietic progenitors are typically quiescent at the onset of culture. Quiescent CFC would not be expected to exhibit high lactate production rates. Thus, the proposed model would be expected to only describe lactate production for cells that have exited quiescence. This is not a major limitation because cells typically leave quiescence within 24 to 48 hours of culture (Traycoff et al., *Exp Hematol*, 22, 1264–1272 (1994)). Indeed, linear regressions of the FIG. 6 data for CD34+ cell cultures describe the relationship between % CFC and $q_{lac}$ reasonably well after the first time point in the culture, which is associated with the lag phase, is removed (FIG. 9).

The proposed model could be used to predict the total CFC content if all cultures had the same values for $\alpha_{lac}$ and $\beta_{lac}$. However, these parameters vary with culture conditions such as cytokine combination, inoculum density, and cell type. It is more likely that the same $\alpha_{lac}$ and $\beta_{lac}$ values will be obtained for samples with similar CD34+ cell content cultured under identical conditions. Indeed, when three different PB MNC samples with similar day zero CD34+ cell content were cultured under identical conditions, the values for $\alpha_{lac}$ and $\beta_{lac}$ were similar enough that the data could be pooled into one correlation, as shown in FIG. 10. The data demonstrate that changes in the CFC content of a culture can be followed by monitoring $q_{lac}$. A correlation between $q_{lac}$ and % CFC was evidenced over a wide variety of conditions, including spinner flask (FIGS. 1, 3, 4, 5) and T-flask (FIGS. 2, 6) cultures with MNC (FIGS. 1, 2, 3, 4, 5) and CD34+ cells (FIG. 6) in serum-containing (FIGS. 3, 6) and serum-free media (FIGS. 1, 2, 4, 5) with different cytokines (FIGS. 4, 5) and inoculum densities (FIGS. 3, 6).

The coincidence of maximum % CFC with maximum $q_{lac}$ may be useful in deciding when to manipulate a hematopoietic culture. For example, for some applications of gene therapy using ex vivo expanded cells, it might be best to initiate gene transfer when the progenitor cell content is highest (i.e., the time of maximum % CFC and $q_{lac}$). However, if the expanded cells are to be used directly for transplantation, it will likely be more beneficial to harvest when the total content of CFC reaches a maximum. Any particular clinical protocol is likely to be restricted to a single cell type (PB or CB; MNC or CD34+ cells), culture system, cytokine combination, and inoculum density. The correlation shown in FIG. 10 indicates that it will be possible to identify unique $\alpha_{lac}$ and $\beta_{lac}$ values for these cultures, or at least distinct $\alpha_{lac}$ and $\beta_{lac}$ values for different ranges of CD34+ cell content in MNC cultures. Since the CD34+ cell content is routinely measured for hematopoietic cell harvests, this means that the appropriate $\alpha_{lac}$ and $\beta_{lac}$ values would be available at the beginning of each culture. In this event, it should be possible to determine the total CFC content (from equation 4), as well as the % CFC (from equation 6), at any time point in the culture, thereby realizing real-time determination of CFC content in culture.

A two-population model also provides an adequate description of glucose consumption. See FIGS. 11A–B and 12A–B. Equations for the two-population model for glucose are:

$$Q_{gluc} = \alpha_{gluc}[CFC] + \beta_{gluc}(X_i - [CFC]) \quad (7)$$

$$\frac{Q_{gluc}}{X_i} = (\alpha_{gluc} - \beta_{gluc})\frac{[CFC]}{X_i} + \beta_{gluc} \quad (8)$$

$$q_{gluc} = (\alpha_{gluc} - \beta_{gluc})\frac{\% \, CFC}{100} + \beta_{gluc} \quad (9)$$

where $\alpha_{gluc}$ is the $q_{gluc}$ value for a CFC, $\beta_{gluc}$ is the $q_{gluc}$ value for a non-CFC, $X_i$ is the concentration of total nucleated cells in the culture, and [CFC] is the concentration of total CFC in the culture.

Example 2

The successful application of spinner flask culture for hematopoietic cells from a variety of sources in both serum-containing and serum-free media was described in Example 1. Spinner flask systems have also been used to culture bone marrow mononuclear cells (BM MNC) (Zandstra et al., *Bio/Technology*, 12, 909–914 (1994); Sardonini and Wu, *Biotechnol. Prog.*, 9, 131–137 (1993)).

A well-controlled, closed, and reproducible culture environment, such as that offered by stirred bioreactors, will undoubtedly prove advantageous for clinical applications, especially considering the scale involved for clinical cultures. The culture volume employed for recent clinical trials averaged about 5 liters (Zimmerman et al., *J. Hematotherapy*, 4, 527–529 (1995); Williams et al., *Blood*, 87, 1687–1691 (1996)). Fifty (50) T-150 flasks each containing 100 ml culture medium or 20 gas-permeable 300 cm² culture bags each containing 250 ml would be necessary to accommodate this volume. These phase I clinical trials were conducted to determine the safety of infusing expanded cells. As trials continue, greater numbers of cells will undoubtedly be transfused in an effort to increase the efficacy of expansion protocols. Although peripheral blood (PB) MNC-derived natural killer (NK) cells have been cultured in a stirred bioreactor (Pierson et al., *J. Hematotherapy*, 5, 475–483 (1996)), controlled, stirred-tank bioreactor systems have not yet been reported for the culture and characterization of myeloid-lineage hematopoietic cells.

In this example, the effects of different hematopoietic populations (CFC and more mature cells) on oxygen consumption, glucose consumption, and lactate production, and on the ratio of glycolytic to oxidative metabolism were examined. Also, culturing hematopoietic cells in bioreactors was investigated.

A. Materials and Methods

Medium. HLTM (see Example 1) was used as the culture medium. HLTM was supplemented with purified recombinant human cytokines: 5 ng/ml IL-3 (Novartis, East Hanover, N.J.), 50 ng/ml IL-6 (Novartis), 50 ng/ml SCF (Amgen), 1.5 ng/ml G-CSF (Amgen), 2 ng/ml GM-CSF (Immunex), and 28 ng/ml Epo (Amgen).

Cells and Cell Separation Procedures. Patient samples (Response Oncology) of mobilized PB MNC were collected as described in Example 1. Apheresis products were also collected as described in Example 1. Samples in 15-ml polystyrene test tubes containing anticoagulant citrate dextrose were stored and shipped under ambient conditions and used as received within 2–3 days of collection; enrichment of the MNC fraction was not required due to minimal erythrocyte content. CB samples were provided by Northwestern University Memorial Hospital (Chicago, Ill.). Erythrocytes were depleted from the whole sample by ammonium chloride lysis (Denning-Kendall et al., *Exp. Hematol.*, 24:1394–1401 (1996)). All samples were incubated for 2–4 days at 1.2–2×10⁶ cells/ml in T-150 flasks (Falcon, Lincoln Park, N.J.) prior to inoculation in either a T-75 flask or a stirred bioreactor. This pre-incubation period, which may prove not to be necessary, was designed to acclimate the cells to the culture conditions of the experiment in the absence of potential fluid-mechanical damage. In addition, it allowed a lag phase to be avoided by transferring exponentially-growing cells into the bioreactor. The number of nucleated cells was determined on a Coulter Counter Multisizer after cetrimide treatment to lyse the cells and release the nuclei.

Methylcellulose Colony Assays. The numbers of granulocyte and monocyte/macrophage (collectively CFU-GM), and erthyroid (BFU-E) progenitor cells (colony-forming cells, or CFC) were determined using the methylcellulose colony assay described in Example 1.

Culture Conditions. Stirred bioreactor cultures were carried out in a 400-ml B. Braun Biostat Q (B. Braun Biotech USA, Allentown, Pa.) with an agitation rate of 30 rpm at a working volume of 150–200 ml. The reactor's stainless steel agitator assembly was removed because detrimental effects of stainless steel on hematopoietic cell proliferation have been observed (LaIuppa et al., *Journal of Biomedical Materials Research*, 36:347–359 (1997). A Bellco spinner flask model 1965–250 agitator assembly was fitted into a compression fitting on the headplate of the reactor. The inside diameter of the Biostat Q is the same as that for the Bellco spinner flask model 1967–100 used in Example 1. The agitation setup was therefore identical (except for the longer agitator shaft) to that employed ($d_i/D=0.8$) in spinner flasks in Example 1. The reactor was maintained within a 37° C. incubator and was fitted with dissolved oxygen (DO, Ingold, Wilmington, Mass.) and pH (Ingold) probes, which were interfaced to a personal computer (PC) via the Workbench PC program (Omega, Stamford, Conn.). DO was controlled at 50% of air saturation through headspace addition of humidified $O_2$, $N_2$, and air. pH was controlled at 7.33±0.03 through headspace addition of humidified $CO_2$. Static cultures were carried out in T-75 flasks (Falcon, Lincoln Park, N.J.) maintained at 37° C. inside a 5% $CO_2$ (balance air) incubator.

Feeding Protocols. The cultures in Experiment 1 were fed every 2 days, beginning at day 4, by pipette removal of one half of the cell suspension, centrifugation at 300×g for 10 minutes, removal of the spent medium, and return of the cells with fresh equilibrated medium to the culture vessel, thereby maintaining a constant culture volume. This feeding protocol was used in the spinner-flask and T-flask culture systems for PB and CB MNC (see Example 1) and is designated Feeding Protocol 1 (FP1). In subsequent experiments, cultures were diluted daily (Experiments 3 and 4) or every two days (Experiment 2) to a density of 1.5–2× 10⁶ cells/ml. Practically, 25–45% of the culture broth (depending on the measured cell density) was removed and the reactor replenished with fresh medium (Feeding Protocol 2, FP2). T-flask controls were fed with a volumetric exchange equivalent to that in the bioreactor. Cell expansion ratios were calculated by determining the total cells that would have been produced in the vessel, assuming that the removed cells expanded in an identical manner as the remaining cells. Medium supernatant samples were frozen at −20° C. and retained for metabolite analysis.

Metabolic Assays and Calculations. Medium supernatant samples were thawed and subsequently analyzed on a YSI model 2700 glucose/lactate analyzer as described in Example 1. Specific glucose and lactate metabolic rates (q, umole/cell/hr) at any time $t_i$ were calculated as follows:

$$q_i = \frac{(t_{i+1} - t_i)\left(\frac{Q_b}{X_b}\right) + (t_i - t_{i-1})\left(\frac{Q_f}{X_f}\right)}{(t_{i+1} - t_{i-1})} \quad (10)$$

$X_b$ and $X_f$ are the log-mean average cell densities for the time periods before and after time i. The log-mean cell density is the effective average cell density. It takes into account the fact that cell density increases exponentially with time. $X_b$ and $X_f$ are calculated as follows:

$$X_b = \frac{X(t_i^{bd}) - X(t_{i-1}^{ad})}{\ln\left(\frac{X(t_i^{bd})}{X(t_{i-1}^{ad})}\right)} \quad (11)$$

-continued $$X_f = \frac{X(t_{i+1}^{bd}) - X(t_i^{ad})}{\ln\left(\frac{X(t_{i+1}^{bd})}{X(t_i^{ad})}\right)} \quad (12)$$

where the superscripts "bd" and "ad" represent the cell density before and after dilution, respectively. $Q_b$ is the point-to-point volumetric glucose consumption or lactate generation rater $$\left(\frac{\mu mole}{ml \cdot hr}\right)$$

from time $t_{i-1}$ to $t_i$ and $Q_f$ is point-to-point rate from time $t_i$ to $t_{i+1}$. For example, for lactate:

$$Q_b = \frac{[\text{lactate}](t_i^{bd}) - [\text{lactate}](t_{i-1}^{ad})}{t_i - t_{i-1}} \quad (13)$$

$$Q_f = \frac{[\text{lactate}](t_{i+1}^{bd}) - [\text{lactate}](t_i^{ad})}{t_{i+1} - t_i} \quad (14)$$

where the superscripts "bd" and "ad" represent the lactate concentration before and after dilution, respectively. Similar equations apply for glucose consumption. The specific glucose and lactate metabolic rates were calculated in this manner because of the abrupt changes in cell density at each dilution step associated with FP2 (see FIG. 14) which did not occur with FP1.

The general relation describing the change in oxygen concentration in the culture medium with time (t) is given by:

$$\frac{dC_{O2}}{dt} = K_L a(C_{O2^*} - C_{O2}) - Q_{02} \quad (15)$$

where $C_{O2}$ is the oxygen concentration in the liquid ($\mu$mole/ml), $C_{O2}^*$ is the liquid oxygen concentration ($\mu$mole/ml) in equilibrium with the headspace gas, $K_L a$ ($hr^{-1}$) is the volumetric mass transfer coefficient, and $Q_{02}$ is the volumetric oxygen uptake rate ($\mu$mole/ml/hr) by cells in the culture. The Henry's coefficient for oxygen in water (atm·l/mmole) is used to calculate $C_{O2}^*$ from the partial pressure of oxygen in the headspace and to calculate $C_{O2}$ from the DO probe reading (the % of air saturation value is first converted to oxygen partial pressure).

The specific oxygen uptake rate ($q_{o2}$, $\mu$mole/cell/hr) was determined for Experiments 1 and 2 using the steady-state method described in Miller et al., *Bioprocess Engineering* 3:103–111 (1988), the complete disclosure of which is incorporated herein by reference. Briefly, DO was measured using the DO probe. The volumetric mass transfer coefficient, $K_L a$, was experimentally determined for cell-free medium by following the increase (or decrease) in oxygen concentration when air (or nitrogen) was passed through the vessel headspace. The oxygen concentration in the vessel headspace was determined using the gas flow rates obtained from calibrated rotameters. At steady-state, the derivative term in equation (15) is equal to zero, so that:

$$Q_{02} = K_L a (C_{O2}^* - C_{O2}) \quad (16)$$

The specific oxygen uptake rate, $q_{02}$ is calculated from the $Q_{02}$ as follows:

$$q_{o2} = Q_{02}/X_i \quad (17)$$

where $X_i$ is the total cell concentration at the time that $Q_{02}$ is determined.

The specific oxygen uptake rate ($q_{o2}$, $\mu$mole/cell/hr) was determined for Experiments 3 and 4 using the dynamic method described in Zhou and Hu, *Biotechnol. Bioeng.*, 44:170–177 (1994), the complete disclosure of which is incorporated herein by reference, using a computer (PC) for data acquisition and control and to perform calculations. Briefly, $Q_{02}$ was first determined. To do so, DO was increased to 65% of saturation with air. Then, nitrogen gas was flushed into the culture vessel to deplete the oxygen from the gas in the headspace, and DO was allowed to decrease until reaching 30% of saturation. The time profile of DO between 50% and 30% was used to calculate $Q_{02}$ using equation (15). Equation (15) can be solved by integration as:

$$Q_{02} = \frac{C_{O2}(t_O) - C_{O2}(t_f)}{t_f - t_O} = \frac{\int_{t_O}^{t_f} K_L a[C_{O2^*} - C_{O2}(t)]dt}{t_f - t_O} \quad (18)$$

where $C_{O2}(t_0)$ is the $C_{O2}$ at the beginning of taking the reading ($t_0$) and $C_{O2}(t_f)$ is the $C_{O2}$ at the end ($t_f$). Since the headspace is swept with nitrogen during the measurement, $C_{O2}^*$ is set to zero in equation (18). $K_L a$ was measured with cell-free medium before the cultivation, as described above. The specific oxygen consumption rate ($q_{o2}$) was calculated from the $Q_{02}$ and the total cell concentration ($X_i$) using equation (17).

For Experiments 3 and 4, $q_{o2}$ was also calculated using the steady-state method on a number of occasions. Good agreement between the two calculation methods was noted.

The ratio of the lactate production rate to the oxygen consumption rate ($Y_{lac,ox}$) was calculated as:

$$Y_{lac,ox} = \frac{q_{lac}}{q_{o2}} \quad (19)$$

B. Results

Effect of Culture System and Feeding Protocol on Total Cell and CFU-GN Expansion. The first bioreactor experiment utilized FP1; the total cell and CFU-GM expansion ratios for this experiment are shown in FIGS. 13A–B. The bioreactor and T-flask had comparable total cell expansion profiles until day 6, when the total cell concentration in both cultures appeared to have plateaued. On day 6, in an effort to increase the culture growth rate, the bioreactor cell density was diluted from $5.2 \times 10^6$ cells/ml to $3.2 \times 10^6$ cells/ml, while the T-flask cell density ($5.1 \times 10^6$ cells/ml) was not changed. The bioreactor was fed using FP1 both before and after this single dilution event. After the dilution, the rate of total cell expansion in the bioreactor increased again (as it did in the T-flask, although to a lesser extent) and a separation was evident between the performance of the two vessels.

It was hypothesized that a dilution-feeding protocol, such as FP2, would increase the extent of total cell expansion in the cultures. FP2 was, therefore, utilized for both the T-flask and the bioreactor in subsequent experiments. FIG. 14 shows the cell density in a CB MNC experiment (Experiment 3) utilizing FP2 throughout the culture period. Through repeated dilution and feeding, cell growth was maintained for an extended period of time in both the reactor and the T-flask. As suspected, FP2 resulted in a much greater expansion of total cells in both vessels (FIGS. 15A–C) than did FP1 (FIG. 13A). If the expansion product is to be infused into a patient for the purpose of re-constituting the hematopoietic system following chemotherapy, CFU-GM cells are likely to be particularly important, since they give rise to critical infection-fighting granulocytes. CFU-GM expansion in FP2-fed systems (FIGS. 16A–C) was much greater than that observed in either the bioreactor or T-flask FP1-fed cultures (FIG. 13B).

Metabolic Rates in the Bioreactor. FIGS. 17A–D show specific lactate ($q_{lac}$) and oxygen ($q_{o2}$) metabolic rates, along with culture CFC content, for the four bioreactor cultures. For the FP1-fed culture (FIG. 17A), the time of maximum $q_{lac}$ corresponds closely with the time of maximum % CFC and the decreasing CFC content is paralleled by decreasing $q_{lac}$ values. These observations are consistent with those from previous experiments that utilized FP1 (see Example 1). In the current work, a similar trend for $q_{o2}$ was observed, although the time of maximum $q_{o2}$ was delayed slightly beyond that for $q_{lac}$.

However, the times of maximum $q_{lac}$ and % CFC did not always correspond for the FP2 cultures. The first FP2-fed CB MNC culture (FIG. 17B) did exhibit an initial correspondence (through 120 hours) between CFC content and $q_{lac}$, although qiac did not decrease to a low level and a significant secondary rise in $q_{lac}$ was observed. The sole PB MNC culture (FIG. 17D) exhibited good correspondence between $q_{lac}$ and % CFC. In contrast, the $q_{lac}$ trend observed for the CB MNC culture shown in FIG. 17C is quite different. Although an increase in $q_{lac}$ after 150 hours is noted in FIGS. 17A, 17B, and possibly 17D, it follows an earlier peak in $q_{lac}$. In FIG. 17C $q_{lac}$ increases steadily from the beginning of the culture and is still increasing at the end of the culture period.

Interestingly, $q_{o2}$ shows a much smaller (if any) secondary increase after the initial decline. As a result, the $q_{o2}$ profile more closely corresponds to the % CFC profile than does the $q_{lac}$ profile for the FP2 cultures.

The $q_{lac}$ and $q_{o2}$ profiles in the bioreactor suggest two things: (1) that cell types other than CFC may impact metabolic rates, particularly $q_{lac}$, and (2) that the extent to which different metabolic pathways are utilized for energy generation changes with cell differentiation. The ratio of lactate production to oxygen consumption ($Y_{lac,ox}$) was, therefore, examined. Higher $Y_{lac,ox}$ values indicate a shift to glycolytic energy production, while lower $Y_{lac,ox}$ values suggest increased utilization of oxidative phosphorylation. FIGS. 18A–D show the profiles for $Y_{lac,ox}$, along with the % CFC for each culture. In general, $Y_{lac,ox}$ dropped from a high value early in culture and reached a minimum when the % CFC began to plateau at a low value. Thereafter, $Y_{lac,ox}$ increased again, which suggests that post-progenitor cells rely to a greater extent on glycolysis for their energy needs. Indeed, in the one experiment analyzed using flow cytometry (FIG. 18C), the increase in $Y_{lac,ox}$ (and $q_{lac}$, FIG. 17C) was paralleled by an increase in the total percentage of CD11b$^+$ and/or CD15$^+$ cells. Post-progenitor cells of the granulomonocytic (GM) lineage, such as developing and mature monocytes and granulocytes, are included in the CD11b$^+$ and CD15$^+$ populations. It was observed that the yield of lactate from glucose ($q_{lac}/q_{gluc}$) increased after 150 hours in culture (data not shown), further supporting the idea that post-CFC more extensively utilize glycolysis for energy production.

C. Discussion

It has previously been demonstrated that both CB and PB MNC can be cultured in spinner flasks under a variety of conditions (see Example 1). Here, it has been demonstrated that a bioreactor vessel can be adapted to provide an acceptable culture environment for hematopoietic cells. As far as is known, this is the first report of a stirred bioreactor with pH and DO control being used for the expansion of myeloid-lineage hematopoietic cells. This work, therefore, represents the next step in the evolution of hematopoietic culture from static systems to spinner culture to a fully-instrumented, stirred bioreactor. Total cell expansion in the bioreactor was similar to that for past experiments in spinner flasks using the cell-retention (FP1) feeding protocol. However, CFU-GM expansion for the sample used in Experiment 1 was less than the ~15-fold expansion typically observed in spinner flasks for CB MNC using FP1 (not shown).

Frequent, dilution-type feeding (FP2) increased the expansion of total cells and CFU-GM, relative to using the FP1 feeding protocol, for CB MNC cultures (Table 1 and data not shown for FP1 spinner-flasks). Similarly, the maximum expansion of total cells and CFU-GM for the one PB MNC FP2 bioreactor culture (Experiment 4) were greater than those in PB MNC FP1 spinner-flask controls (Table 1). Dilution-type feeding protocols have been utilized for static CD34$^+$ cell cultures by many researchers (Moore and Hoskins, *Blood Cells*, 20:468–79 (1994); Lill et al., *Stem Cells*, 12:626–637 (1994); Haylock et al., *Blood*, 80:1405–1412 (1992)), with total cell expansion ratios that often exceed 1,000. In static cultures of MNC and CD34$^+$ cells, expansion ratios and the kinetics of expansion are highly dependent on the cell inoculum density (ID) (Koller et al., *Biotechnol. Bioeng.*, 50:505–513 (1996); Haylock et al., in: *Hematopoietic stem cells: biology and therapeutic applications* (D. Levitt et al., eds., Marcel Dekker, Inc., New York, pp. 491–517 (1995)). In general, lower ID leads to greater total cell expansion and greater depletion of CFC. Higher ID cultures achieve greater total cell and CFC numbers, but a lower total cell expansion ratio, when compared to lower ID cultures. Perhaps due to the high residual cell density (1.5–2×10$^6$ cells/ml) in our FP2 cultures, increased total cell expansion did not come at the expense of CFU-GM depletion. As shown in Table 1, the maximum observed percentages of CFU-GM (cloning efficiency) in the FP2 cultures were much greater than those observed for the FP1 bioreactor culture (CB MNC) or spinner-flask controls (PB MNC).

Increased total cell production with no decrease (or even an increase) in CFC production suggests that feeding by dilution released the cells from a "blocked" state—perhaps induced by accumulation of endogenous cytokines or inhibitory metabolites in FP1 cultures, which reach 6–12×10$^6$ cells/ml. Although the underlying mechanisms are not well understood, decreased metabolic activity in high-density cultures has previously been reported for cells of hematopoietic origin, and has been termed a "crowding" effect (Sand et al., *Blood*, 50:337–346 (1977)). Additional evidence for the concept of release from inhibition is provided by differences in the lactate production pattern for FP2 cultures, with a secondary increase in $q_{lac}$ after the decline in % CFC (see below).

For FP2, total cell (FIGS. 15A–C) and CFU-GM (FIGS. 16A–C) expansion were similar in the bioreactor and T-flask cultures. In contrast, using FP1 superior total cell and CFU-GM expansion was observed in stirred (spinner) vessels vs. T-flasks for PB MNC cultures inoculated with 1.2×10$^6$ cells/ml (see Collins et al., *Biotechnol. Bioeng.*, 59:534–43 (1998), the complete disclosure of which is incorporated herein by reference). BM MNC cultures in perfused T-flasks benefit (in terms of total cell and CFU-GM expansion) from a similar dilution-feeding protocol (Oh et al., *Biotechnol. Bioeng.*, 44:609–616 (1994)). In that perfused T-flask system, repeated cell removal increased the available culture surface area and alleviated mass transfer limitations. Similarly, the enhanced mass transfer in stirred culture will minimize gradients in DO and pH (by increased $CO_2$ removal), as well as inhibitory cytokines that may accumulate in the cultures. The beneficial effect of increased mass transfer is less important at lower cell densities, as evidenced by similar total cell and CFU-GM expansion in spinner flasks vs. T-flasks using FP1 in PB MNC cultures inoculated with $2\times10^5$ cells/ml (see Collins et al., *Biotechnol. Bioeng.*, 59:534–43 (1998). Thus, by frequently diluting the cell density in the FP2 experiments reported here, the benefit of stirred culture on cell and CFU-GM production was offset. This is consistent with the observation that the benefit of increasing medium exchange rate in static BM MNC cultures is greater at higher ID (Koller et al., *Biotechnol. Bioeng.*, 50:505–513 (1996). Together, these observations suggest that a controlled cell density is indeed beneficial for the proliferation of hematopoietic cultures.

It was previously demonstrated that CFC consume more glucose and generate more lactate on a per cell basis than do more mature cells (see Example 1). Here it is shown that oxygen consumption is also higher for CFC (FIGS. 17A–D). The $q_{o2}$ values for our stirred cultures ranged from $1.7\times10^{-8}$ to $1.2\times10^{-7}$ μmole/cell/hr. The highest values are slightly lower than the $1-3\times10^{-7}$ μmole/cell/hr reported for hybridomas (Wohlpart et al., *Biotechnol. Bioeng.*, 37:1050–1053 (1991); McQueen and Bailey, *Biotechnol. Bioeng.*, 35:1067–1077, (1990); Glacken et al., *Biotechnol. Bioeng.*, 32:491–506 (1988); Miller et al., *J. Cell. Physiol.*, 132:524–530 (1987)), and are much higher than the $1-4\times10^{-8}$ μmole/cell/hr reported for murine bone marrow cells (Lutton et al., *Experientia*, 28:850 (1972); Olander, *American Journal of Physiology*, 222:45–48 (1972); Gesinski and Morrison, *Experientia*, 24:296–297 (1968); Gesinski et al., *Australian Journal of Biological Sciences*, 21:1319–1324 (1968)), human bone marrow cells (Peng and Palsson, *Annals of Biomedical Engineering*, 24:373–381 (1996), and normal human granulocytes (Bird et al., *Cancer*, 1009–1014 (September 1951)). The values reported for murine cells were obtained in experiments without the growth factor stimulation present in the present cultures. Since growth factor stimulation increases glucose uptake in culture (Whetton et al., *EMBO J.*, 3:409–413 (1984); Whetton et al., *J. Cell Sci.*, 84:93–104 (1986); Spielholz et al., *Blood*, 85:973–980 (1995); Hamilton et al., *Biochem. Biophys. Res. Commun.*, 138:445–454 (1986)), it is likely that cytokine stimulation would also increase $q_{o2}$. The values reported for human BM MNC culture, which are much lower than those reported here, were obtained in growth-factor-supplemented systems (Peng and Palsson, *Annals of Biomedical Engineering*, 24:373–381 (1996). However, some of the $q_{o2}$ values may have been obtained under oxygen-limited conditions, which would decrease the value of $q_{o2}$ (Miller et al., *J. Cell. Physiol.*, 132:524–530 (1987); Sand et al., *Blood*, 50: 337–346 (1977)). Interestingly, the $q_{o2}$ value for normal human granulocytes ($2.2\times10^{-8}$ μmole/cell/hr; Bird et al., *Cancer*, 1009–1014 (September 1951)) is similar to the $q_{o2}$ values that observed here when CFC have been depleted.

For FP1 cultures, a correlation between $q_{lac}$ and % CFC is almost always observed—with a close correspondence between the maxima in $q_{lac}$ and % CFC and a low value for $q_{lac}$ after the CFC are depleted (see Example 1). For most FP2 cultures, there was still a maximum in $q_{lac}$ near the maximum in % CFC, but in both FP2 CB MNC cultures there was a secondary increase in $q_{lac}$ that exceeded the initial peak value. This suggests that GM post-progenitors can also exhibit significant glycolytic activity, and that the correlation between $q_{lac}$ and % CFC developed for FP1 cultures is not fully valid for FP2 cultures. However, this is not as great a limitation as it may seem because $q_{o2}$ does not exhibit a significant secondary peak after the peak in % CFC (FIGS. 17A–D). This suggests that GM post-progenitors are highly glycolytic, but do not have high oxidative metabolic activity. In this regard, the % of cells that stained positive for CD15 and/or CD11b (GM markers) increased proportionally with $Y_{lac,ox}$ in one CB MNC FP2 culture analyzed by flow cytometry (FIG. 18C). Although flow cytometry analysis for the other bioreactor experiments was not performed, similar increases in $Y_{lac,ox}$ were observed. Both monocytes and granulocytes developed concurrently in Experiment 3; therefore, determining which cell type had the largest effect on $Y_{lac,ox}$ and $q_{lac}$ is difficult. Previous work with monocytes (Cline, in *Formation and Destruction of Blood Cells*, pages 222–239 (Greenwalt and Jamieson eds., 1970)) has shown that these cells rely heavily upon glycolysis for their energy needs. Cultures supplemented with Flt3-1 and macrophage-colony stimulating factor (M-CSF) have been demonstrated to produce nearly pure populations of monocytes (Gabbianelli et al., *Blood*, 86, 1661–1670 (1995)). Under these culture conditions (using FP1), steadily increasing $q_{lac}$ and % CFC have been observed (see Example 1), trends similar to those shown in FIG. 17C. Finally, other reports indicate that granulocytes have very few mitochondria (Bainton et al., *J. Exp. Med.*, 134, 907–934 (1971)) and would, therefore, not consume much oxygen.

The control of pH, DO, and other physicochemical parameters in a stirred bioreactor will allow for more refined studies regarding the effects of these parameters on hematopoietic cells. Production of the large numbers of hematopoietic cells desired for clinical applications may well benefit from feeding protocols that help control the concentration of all species in a culture. Stirred bioreactor systems are readily adaptable to perfusion feeding protocols, which allow for extensive medium replacement while maintaining a high cell density. The results indicate that monitoring metabolic quotients for oxygen, lactate, and other metabolites will allow practitioners to estimate the percentages of CFC in culture.

TABLE 1

Maximum observed total cell expansion, CFU-GM expansion, and % CFU-GM for FP1 and FP2 cultures.

|  | Maximum Total Cell Expansion | Maximum CFU-GM Expansion | Maximum % CFU-GM |
|---|---|---|---|
| CB MNC |  |  |  |
| Experiment 1 (FP1) Bioreactor/T-flask | 9.9/6.4 | 1.6/4.7 | 1.1/1.4 |
| Experiment 2 (FP2) Bioreactor/T-flask | 34.2/26 | 23.5/23.7 | 4.71/4.6 |
| Experiment 3 (FP2) Bioreactor/T-flask | 201/207 | 29/33 | 3.2/3.05 |
| PB MNC |  |  |  |
| Control[a] Spinners (FP1) | 14.4 ± 6.1 | 6.8 ± 3.2 | 1.61 ± 0.33 |
| Experiment 4 Bioreactor (FP2) | 397 | 13.5 | 5.6 |

[a]The control value is the average ± 1 SEM for 5 (n = 5) PB MNC spinner flask cultures carried out in HLTM + IL-3, IL-6, SCF, G-CSF, GM-CSF, and Epo at an ID of 2.15 ± 0.09 x $10^5$ cells/ml. The controls were fed using FP1 and represent the typical expansion seen in this type of system.

D. Modeling Cell Metabolism

As demonstrated in Example 1, $q_{lac}$ and % CFC can be related with a linear model when using FP1. The results obtained in this example for $q_{o2}$ suggested that a similar relationship might be obtained for $q_{o2}$ and % CFC for both FP1 and FP2. Utilizing the same model as for $q_{lac}$ (see Example 1, section H), but substituting $q_{o2}$ for $q_{lac}$, the following equation was obtained:

$$q_{o2} = (\alpha_{o2} - \beta_{o2})\frac{\% \ CFC}{100} + \beta_{o2} \quad (20)$$

where, $\alpha_{o2}$ is the $q_{o2}$ for an average CFC and $\beta_{o2}$ is the $q_{o2}$ for the average non-CFC.

This model was tested on the data of the bioreactor experiments, and the results are shown in FIGS. 19A–D. In FIGS. 19A–D, $q_{o2}$ is plotted versus % CFC. The $q_{o2}$ corresponding to the first time point (~24 hours) for the plots of experiments 1 and 2 (FIGS. 19A and 19B) was eliminated from the model analysis. These $q_{o2}$ values were much lower than expected for the corresponding % CFC. This may reflect an incomplete exit from quiescence at the time of this first measurement, which was a problem for the lactate model when applied to CD34+ cells. The $q_{o2}$ corresponding to the third time point (~96 hours) for the plot of Experiment 3 (FIG. 19C) was also eliminated from the model analysis. This point appears to be an outliner as compared to the remaining data and as compared to all other experiments' $q_{o2}$ profiles. The straight lines shown in FIGS. 19A–D were generated by linear regression. In these graphs, the y-intercepts correspond to $\beta_{o2}$ (the $q_{o2}$ for the average non-CFC), and the slopes of the lines yield the differences between $q_{o2}$ for a CFC and that for a non-CFC.

As can be seen, the model described oxygen consumption well for the data that were fit for both FP1 and FP2. It is expected, therefore, that the oxygen model will prove to be reliable for determining % CFC over a wide range of culture conditions.

Also, $Q_{o2}$ and total CFC can be related by the following equation:

$$Q_{o2} = \alpha_{o2}[CFC] + \beta_{o2}(X_i - [CFC]) \quad (21)$$

We claim:

1. A method of determining the content of progenitor cells in a hematopoietic cell culture, the method comprising:
   culturing a reference culture of hematopoietic cells under selected conditions, the selected conditions comprising employing a selected feeding protocol;
   measuring one or more metabolic parameters selected from the group consisting of glucose consumption, lactate production and oxygen consumption of the reference culture at a plurality of selected times;
   determining the content of progenitor cells in the reference culture at each of the selected times;
   culturing an experimental culture of hematopoietic cells under essentially the same conditions used to culture the reference culture;
   measuring the same one or more metabolic parameters for the experimental culture at one or more selected time(s) as measured for the reference culture; and
   comparing the one or more metabolic parameters measured for the experimental culture with those measured for the reference culture to determine the content of progenitor cells in the experimental culture at the selected time(s).

2. The method of claim 1 wherein the selected conditions comprise culturing bone marrow mononuclear cells, cord blood mononuclear cells, or peripheral blood mononuclear cells.

3. The method of claim 1 wherein the selected conditions comprise culturing a cell population from bone marrow, cord blood or peripheral blood that is enriched in CD34+ cells.

4. The method of claim 1 wherein the selected conditions comprise using a combination of cytokines that causes expansion of total cells, progenitor cells, post-progenitor cells or combinations thereof.

5. The method of claim 1 wherein the selected conditions comprise using at least one cytokine from each of the following groups:
   i. cytokines acting on primitive hematopoietic cells; and
   ii. cytokines acting on a wide array of progenitor cells.

6. The method of claim 5 wherein the selected conditions further comprise using at least one additional cytokine from the following additional group:
   iii. cytokines acting on lineage-restricted hematopoietic cells.

7. The method of claim 1 wherein the selected conditions comprise using at least one cytokine from each of the following groups:
   i. stem cell factor or Flt3 ligand;
   ii. interleukin-3, interleukin-6, or granulocyte-macrophage colony stimulating factor; and
   iii. granulocyte colony stimulation factor or erythropoietin.

8. The method of claim 1 wherein the selected conditions comprise using serum-free culture medium.

9. The method of claim 1 wherein the selected conditions comprise using serum-containing culture medium.

10. The method of claim 1 wherein the selected conditions comprise stirring the culture.

11. The method of claim 10 wherein the stirred culture is performed in a bioreactor.

12. The method of claim 1 wherein the selected conditions comprise not stirring the culture.

13. The method of claim 1 wherein the selected conditions comprise using a feeding protocol which comprises adjusting the cell density of the culture at least every other day to a selected level so as to optimize the production of cells.

14. The method of claim 13 wherein the cell density is adjusted daily to about $1.5$–$2.0 \times 10^6$ cells/ml.

15. The method of claim 1 wherein the selected conditions comprise using a feeding protocol which comprises replacing about 50% of the culture medium, with cell retention, every other day beginning about 4 days after initiation of the culture.

16. A method of determining colony-forming cell content of a hematopoietic cell culture, the method comprising:
   culturing a reference culture of hematopoietic cells under selected conditions, the selected conditions comprising using a feeding protocol that limits the production of post-progenitor cells that have high glucose consumption and lactate production;
   measuring the total glucose consumption or lactate production per unit volume of the reference culture at a plurality of selected times;
   measuring the density of nucleated cells ($X_i$) present in the reference culture at each of the selected times;
   using the measured $X_i$ and the measured glucose consumption or lactate production to calculate $q_{gluc}$ or $q_{lac}$ at each of the selected times using equations (1) and (2) set forth below:

$$Q_i = \frac{(t_{i+1} - t_i)(\text{slope}_b) + (t_i - t_{i-1})(\text{slope}_f)}{(t_{i+1} - t_{i-1})} \quad (1)$$

wherein:
   $Q_i$ is the total glucose consumed or lactate produced ($\mu$mole/ml/hr) at time $t_i$;

$t_i$ is any time point;

$t_{i+1}$ is a time point after time point $t_i$;

$t_{i-1}$ is a time point before time point $t_i$;

slope$_b$ is the first order backward slope from time $t_{i-1}$ to time $t_i$ of the total glucose consumption or lactate production curve calculated by dividing the point-to-point glucose consumption or lactate production differences by the point-to-point differences in time; and slope$_f$ is the first order forward slope from time $t_i$ to time $t_{i+1}$ of the total glucose consumption or lactate production curve calculated by dividing the point-to-point glucose consumption or lactate production differences by the point-to-point differences in time;

$$q_i = \frac{Q_i}{X_i} \qquad (2)$$

wherein:

$q_i$ is the specific glucose consumption or lactate production rate ($\mu$mole/cell/hr) at time $t_i$; and $t_i$, $Q_i$ and $X_i$ are defined above;

determining the percentage of colony-forming cells (% CFC) in the reference culture at each of the selected times;

using the % CFC and $q_{lac}$ or $q_{gluc}$ to determine $\alpha_{lac}$ and $\beta_{lac}$ or $\alpha_{gluc}$ and $\beta_{gluc}$ using equation (6) or (9) set forth below:

$$q_{lac} = (\alpha_{lac} - \beta_{lac})\frac{\% \ CFC}{100} + \beta_{lac} \qquad (6)$$

wherein:

$q_{lac}$ is the specific lactate production rate;

$\alpha_{lac}$ is the $q_{lac}$ value for a CFC; and $\beta_{lac}$ is the $q_{lac}$ value for a non-CFC;

$$q_{gluc} = (\alpha_{gluc} - \beta_{gluc})\frac{\% \ CFC}{100} + \beta_{gluc} \qquad (9)$$

wherein:

$q_{gluc}$ is the specific glucose consumption rate;

$\alpha_{gluc}$ is the $q_{gluc}$ value for a CFC; and $\beta_{gluc}$ is the $q_{gluc}$ value for a non-CFC;

culturing an experimental culture of hematopoietic cells under essentially the same conditions used to culture the reference culture;

measuring the total glucose consumption or lactate production per unit volume of the experimental culture at a plurality of selected times;

measuring the density of nucleated cells ($X_i$) present in the experimental culture at the selected times;

using the measured $X_i$ and the measured glucose consumption or lactate production to calculate $q_{gluc}$ or $q_{lac}$ for the experimental culture using equations (1) and (2); and using the calculated $q_{lac}$ or $q_{gluc}$ for the experimental culture and the values of $\alpha_{lac}$ and $\beta_{lac}$ or $\alpha_{gluc}$ and $\beta_{gluc}$ for the reference culture to calculate the % CFC at the selected times for the experimental culture using equation (6) or (9).

17. The method of claim 16 wherein lactate production is measured.

18. A method of determining colony-forming cell content of a hematopoietic cell culture, the method comprising:

culturing a reference culture of hematopoietic cells under selected conditions, the selected conditions comprising using a feeding protocol that limits the production of post-progenitor cells that have high glucose consumption and lactate production;

measuring the total glucose consumption or lactate production per unit volume of the reference culture at a plurality of selected times;

measuring the density of nucleated cells ($X_i$) present in the reference culture at each of the selected times;

using the measured $X_i$ and the measured glucose consumption or lactate production to calculate $q_{gluc}$ or $q_{lac}$ at each of the selected times using equations (1) and (2) set forth below:

$$Q_i = \frac{(t_{i+1} - t_i)(\text{slope}_b) + (t_i - t_{i-1})(\text{slope}_f)}{(t_{i+1} - t_{i-1})} \qquad (1)$$

wherein:

$Q_i$ is the total glucose consumed or lactate produced ($\mu$mole/ml/hr) at time $t_i$;

$t_i$ is any time point;

$t_{i+1}$ is a time point after time point $t_i$;

$t_{i-1}$ is a time point before time point $t_i$;

slope$_b$ is the first order backward slope from time $t_{i-1}$ to time $t_i$ of the total glucose consumption or lactate production curve calculated by dividing the point-to-point glucose consumption or lactate production differences by the point-to-point differences in time; and slope$_f$ is the first order forward slope from time $t_i$ to time $t_{i+1}$ of the total glucose consumption or lactate production curve calculated by dividing the point-to-point glucose consumption or lactate production differences by the point-to-point differences in time;

$$q_i = \frac{Q_i}{X_i} \qquad (2)$$

wherein:

$q_i$ is the specific glucose consumption or lactate production rate ($\mu$mole/cell/hr) at time $t_i$; and $t_i$, $Q_i$ and $X_i$ are defined above;

determining the percentage of colony-forming cells (% CFC) in the reference culture at each of the selected times;

using the % CFC and $q_{lac}$ or $q_{gluc}$ to determine $\alpha_{lac}$ and $\beta_{lac}$ or $\alpha_{gluc}$ and $\beta_{gluc}$ using equation (6) or (9) set forth below:

$$q_{lac} = (\alpha_{lac} - \beta_{lac})\frac{\% \ CFC}{100} + \beta_{lac} \qquad (6)$$

wherein:

$q_{lac}$ is the specific lactate production rate;

$\alpha_{lac}$ is the $q_{lac}$ value for a CFC; and $\beta_{lac}$ is the $q_{lac}$ value for a non-CFC;

$$q_{gluc} = (\alpha_{gluc} - \beta_{gluc})\frac{\% \ CFC}{100} + \beta_{gluc} \qquad (9)$$

wherein:

$q_{gluc}$ is the specific glucose consumption rate;

$\alpha_{gluc}$ is the $q_{gluc}$ value for a CFC; and $\beta_{gluc}$ is the $q_{gluc}$ value for a non-CFC;

culturing an experimental culture of hematopoietic cells under essentially the same conditions used to culture the reference culture;

measuring the total glucose consumption or lactate production per unit volume of the experimental culture at a plurality of selected times;

using the measured glucose consumption or lactate production to calculate $Q_{gluc}$ or $Q_{lac}$ at the selected times using equation (1);

measuring the concentration of nucleated cells ($X_i$) present in the experimental culture at the selected times; and using the measured $X_i$ and the calculated $Q_{lac}$ or $Q_{gluc}$ for the experimental culture and the values of $\alpha_{lac}$ and $\beta_{lac}$ or $\alpha_{gluc}$ and $\beta_{gluc}$ for the reference culture to calculate the concentration of total CFC at the selected times for the experimental culture using equation (4) or (7) set forth below:

$$Q_{lac} = \alpha_{lac}[CFC] + \beta_{lac}(X_i - [CFC]) \quad (4)$$

wherein:
$Q_{lac}$ is the total lactate production;
is the concentration of total CFC in the culture; and
$\alpha_{lac}$, $\beta_{lac}$ and $X_i$ are defined above;

$$Q_{gluc} = \alpha_{gluc}[CFC] + \beta_{gluc}(X_i - [CFC]) \quad (7)$$

wherein:
$Q_{gluc}$ is total glucose consumption; and
$\alpha_{gluc}$, $\beta_{gluc}$, $X_i$ and are defined above.

19. A method of determining colony-forming cell content of a hematopoietic cell culture, the method comprising:

culturing a reference culture of hematopoietic cells under selected conditions, the selected conditions comprising employing a selected feeding protocol;

measuring the volumetric oxygen uptake rate ($Q_{O2}$) ($\mu$mole/ml/hr) of the reference culture at a plurality of selected times;

measuring the density of nucleated cells ($X_i$) present in the reference culture at each of the selected times;

using the measured $X_i$ and $Q_{O2}$ to calculate $q_{o2}$ at each of the selected times using equation (17) set forth below:

$$q_{o2} = Q_{o2}/X_i \quad (17)$$

wherein:
$q_{o2}$ is the specific oxygen consumption rate ($\mu$mole/cell/hr); and
$Q_{O2}$ and $X_i$ are defined above;

determining the percentage of colony-forming cells (% CFC) in the reference culture at each of the selected times;

using the % CFC and $q_{o2}$ to determine $\alpha_{o2}$ and $P_{O2}$ using equation (20) set forth below:

$$q_{02} = (\alpha_{02} - \beta_{02})\frac{\% \ CFC}{100} + \beta_{02} \quad (20)$$

wherein:
$\alpha_{o2}$ is the $q_{o2}$ value for a CFC;
$\beta_{O2}$ is the $q_{o2}$ value for a non-CFC; and
$q_{o2}$ is defined above;

culturing an experimental culture of hematopoietic cells under essentially the same conditions used to culture the reference culture;

measuring the $Q_{O2}$ of the experimental culture at one or more selected time(s);

measuring the density of nucleated cells ($X_i$) present in the experimental culture at the selected time(s);

using the measured $X_i$ and $Q_{O2}$ to calculate $q_{o2}$ for the experimental culture using equation (17); and using the calculated $q_{o2}$ for the experimental culture and the values of $\alpha_{o2}$ and $\beta_{o2}$ for the reference culture to calculate the % CFC at the selected time(s) for the experimental culture using equation (20).

20. A method of determining colony-forming cell content of a hematopoietic cell culture, the method comprising:

culturing a reference culture of hematopoietic cells under selected conditions, the selected conditions comprising employing a selected feeding protocol;

measuring the volumetric oxygen uptake ($Q_{O2}$) ($\mu$mole/ml/hr) of the reference culture at a plurality of selected times;

measuring the density of nucleated cells ($X_i$) present in the reference culture at each of the selected times;

using the measured $X_i$ and $Q_{O2}$ to calculate $q_{o2}$ at each of the selected times using equation (17) set forth below:

$$q_{o2} = Q_{o2}/X_1 \quad (17)$$

wherein:
$q_{o2}$ is the specific oxygen consumption rate ($\mu$mole/cell/hr); and
$Q_{O2}$ and $X_i$ are defined above;

determining the percentage of colony-forming cells (% CFC) in the reference culture at each of the selected times;

using the % CFC and $q_{o2}$ to determine $\alpha_{o2}$ and $\beta_{o2}$ using equation (20) set forth below:

$$q_{02} = (\alpha_{02} - \beta_{02})\frac{\% \ CFC}{100} + \beta_{02} \quad (20)$$

wherein:
$\alpha_{o2}$ is the $q_{o2}$ value for a CFC;
$\beta_{O2}$ is the $q_{o2}$ value for a non-CFC; and
$q_{o2}$ is defined above;

culturing an experimental culture of hematopoietic cells under essentially the same conditions used to culture the reference culture;

measuring the $Q_{O2}$ of the experimental culture at one or more selected time(s);

measuring the concentration of nucleated cells ($X_i$) present in the experimental culture at the selected time(s); and using the measured $X_i$ and $Q_{O2}$ for the experimental culture and the values of $\alpha_{o2}$ and $\beta_{o2}$ for the reference culture to calculate the concentration of total CFC at the selected time(s) for the experimental culture using equation (21) set forth below:

$$Q_{o2} = \alpha_{o2}[CFC] + \beta_{o2}(X_i - [CFC]) \quad (21)$$

wherein:
$\alpha_{o2}$ is the $q_{o2}$ value for a CFC;
$\beta_{O2}$ is the $q_{o2}$ value for a non-CFC;
is the concentration of total CFC in the culture; and
$q_{o2}$, $Q_{O2}$ and $X_i$ are defined above.

* * * * *

UNITED STATES PATENT AND TRADEMARK OFFICE
CERTIFICATE OF CORRECTION

PATENT NO.   : 6,077,708
DATED        : June 20, 2000
INVENTOR(S)  : Collins et al.

Page 1 of 1

It is certified that error appears in the above-identified patent and that said Letters Patent is hereby corrected as shown below:

Column 31,
Line 24, at the beginning of the phrase, add -- [CFC]--
Line 31, after "and", please add --[CFC]--

Claim 19,
Line 54, please delete "$P_{02}$" and add -- $\beta_{02}$ -- therefor

Claim 20,
Line 63, at the beginning of the phrase, add -- [CFC] --

Signed and Sealed this

Fourteenth Day of August, 2001

*Attest:*

Nicholas P. Godici

NICHOLAS P. GODICI
*Attesting Officer*   *Acting Director of the United States Patent and Trademark Office*